(12) United States Patent
Maeshima et al.

(10) Patent No.: US 7,781,543 B2
(45) Date of Patent: Aug. 24, 2010

(54) CURABLE ALICYCLIC DIEPOXY RESIN COMPOSITION

(75) Inventors: Hisashi Maeshima, Ohtake (JP); Hideyuki Takai, Ohtake (JP)

(73) Assignee: Daicel Chemical Industries, Ltd., Osaka (JP)

( * ) Notice: Subject to any disclaimer, the term of this patent is extended or adjusted under 35 U.S.C. 154(b) by 0 days.

(21) Appl. No.: 12/314,222

(22) Filed: Dec. 5, 2008

(65) Prior Publication Data

US 2009/0131547 A1 May 21, 2009

Related U.S. Application Data

(62) Division of application No. 10/526,672, filed as application No. PCT/JP03/11287 on Sep. 4, 2003, now abandoned.

(30) Foreign Application Priority Data

| Sep. 5, 2002 | (JP) | 2002-260490 |
| Dec. 13, 2002 | (JP) | 2002-362684 |
| Dec. 25, 2002 | (JP) | 2002-375662 |
| May 16, 2003 | (JP) | 2003-139484 |
| Jun. 16, 2003 | (JP) | 2003-171176 |

(51) Int. Cl.
*C08L 63/00* (2006.01)
*C08L 63/04* (2006.01)

(52) U.S. Cl. .................. 525/533; 525/481; 525/523; 525/524; 525/526

(58) Field of Classification Search .................. None
See application file for complete search history.

(56) References Cited

U.S. PATENT DOCUMENTS

| 3,075,955 A | 1/1963 | Starcher et al. |
| 3,271,371 A | 9/1966 | Tinsley et al. |
| 5,378,736 A | 1/1995 | Fujiwa et al. |
| 5,494,977 A | 2/1996 | Harano et al. |
| 5,985,510 A | 11/1999 | Akutsu et al. |
| 2003/0059618 A1 | 3/2003 | Takai |
| 2004/0242839 A1 | 12/2004 | Takai |

FOREIGN PATENT DOCUMENTS

| DE | 758728 | 11/1953 |
| DE | 1099733 | 2/1961 |
| DE | 1418465 A | 10/1968 |
| DE | 3211305 | 9/1983 |
| EP | 844262 A2 | 5/1998 |
| EP | 0 950 677 | 10/1999 |
| GB | 996064 | 8/1961 |
| GB | 2008593 A | 6/1979 |
| JP | 48029899 | 4/1973 |
| JP | 50-32500 A | 3/1975 |
| JP | 53-35999 A | 4/1978 |
| JP | 54-003006 | 1/1979 |
| JP | 54-3006 A | 1/1979 |
| JP | 58-172387 A | 10/1983 |
| JP | 59-136321 | 8/1984 |
| JP | 61-213204 A1 | 9/1986 |
| JP | 2-169620 A | 6/1990 |
| JP | 5-194716 | 8/1993 |
| JP | 5-239043 A | 9/1993 |
| JP | 5-279451 | 10/1993 |
| JP | 7-45126 | 2/1995 |
| JP | 7-196774 | 8/1995 |
| JP | 9-124767 A1 | 5/1997 |
| JP | 9-176288 A | 7/1997 |
| JP | 11-1631 A1 | 1/1999 |
| JP | 11-106474 | 4/1999 |
| JP | 11-255863 | 9/1999 |
| JP | 2003-109780 | 4/2000 |
| JP | 2003-73457 A1 | 3/2003 |
| JP | 2003 013001 A | 5/2003 |
| JP | 2003-519705 A1 | 6/2003 |
| JP | 2004-99467 A1 | 4/2004 |

(Continued)

OTHER PUBLICATIONS

Hau Yu, Thermosetting Resin, 2nd Issue, pp. 32-33 (1999).

(Continued)

*Primary Examiner*—Robert Sellers
(74) *Attorney, Agent, or Firm*—Birch, Stewart, Kolasch & Birch, LLP

(57) ABSTRACT

An alicyclic diepoxy compound (A) represented by formula (I)

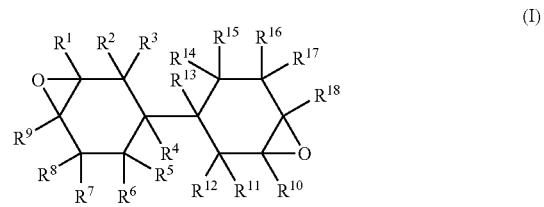

is produced in high purity and high yield at low cost, by epoxidizing the corresponding alicyclic diolefin compound with an organic percarboxylic acid. The curable epoxy resin composition has high reactivity for various curing agents, low viscosity, and excellent workability. A cured product thereof shows useful physical properties for uses in coatings, inks, adhesives, sealants, and encapsulants, etc. It is of extremely high quality as an epoxy resin composition for the encapsulation of electronic parts. A stabilizer for an electrical insulating oil (the alicyclic diepoxy compound or an electrical insulting oil containing the compound) is low in acid value, and the stabilizer improves the properties of the insulating oil. A cured product obtained by curing a casting epoxy resin composition for electrical insulation has excellent properties such as high bending strength, high Tg, and low permittivity.

17 Claims, 1 Drawing Sheet

FOREIGN PATENT DOCUMENTS

| | | |
|---|---|---|
| JP | 2004-182648 A1 | 7/2004 |
| JP | 2004-204228 A | 7/2004 |
| JP | 2004-262874 A1 | 9/2004 |
| WO | WO-00/03300 | 1/2000 |
| WO | WO-02/076966 A1 | 10/2002 |

OTHER PUBLICATIONS

HCAPLUS accession No. 1972:526335 for the Neftekhimiya article by Yur've et al., vol. 12, No. 3, 1972, four pages.

Yur've, V.P: Gailyunas, G.A: Tolstikov, Oxidation of dienes by hydroperoxides. Neftehimiya, 1972, vol. 12, No. 3, p. 353-357.

CURABLE ALICYCLIC DIEPOXY RESIN COMPOSITION

This application is a Divisional of application Ser. No. 10/526,672 filed on Mar. 4, 2005, now abandoned, to which priority is claimed under 35 U.S.C. §120. Application Ser. No. 10/526,672 is the national phase under 35 U.S.C. §371 of PCT International Application No. PCT/JP2003/011287 filed on Sep. 4, 2003; which in turn claims priority to Japanese Applications Nos. 2002-260490, 2002-362684, 2002-375662, 2003-139484, and 2003-171176; filed respectively on Sep. 5, 2002; Dec. 13, 2002; Dec. 25, 2002; May 16, 2003 and Jun. 16, 2003. The entire contents of each of the above-identified applications are hereby incorporated by reference.

TECHNICAL FIELD

The present invention relates to a process for preparation of an alicyclic diepoxy compound in which an unsaturated group-containing compound having a bicyclohexyl-3,3'-diene skeleton is reacted with an organic per carboxylic acid. In addition, the present invention relates to a curable resin composition having such the diepoxy compound as an essential ingredient and to a cured product thereof. The resin composition is useful in various fields including applications such as coatings, ink, adhesives, sealants, and encapsulating materials. Moreover, the present invention relates to an epoxy resin composition for encapsulating electronic parts such as a semiconductor, the epoxy resin composition containing the above alicyclic diepoxy compound as an essential ingredient and showing high moisture-resistance and high fluidity. Moreover, the present invention relates to a stabilizer for an electrical insulating oil and an electrical insulating oil. More particularly, the present invention relates to a stabilizer for an electrical insulating oil and an electrical insulating oil, each of which contains the alicyclic diepoxy compound and has improved long-term stability. Furthermore, the present invention relates to a casting epoxy resin composition for electrical insulation and a cured product thereof, the casting epoxy resin composition having low viscosity and highly workable properties and essentially containing an epoxy resin composition that contains the alicyclic diepoxy compound, an inorganic filler, and the like.

BACKGROUND ART

Currently, various types of multifunctional epoxy compounds (hereinafter, also referred to as epoxy resins) each having two or more alicyclic skeletons in the molecule are commercially available. Examples thereof include: 3,4-epoxycyclohexylmethyl-3',4'-epoxycyclohexanecarboxylate (e.g., CELLOXIDE 2021 manufactured by Daicel Chemical Industries, Ltd., ERL4221 manufactured by Union Carbide Corporation, etc.); 1,2,8,9-diepoxylimonene (e.g., CELLOXIDE 3000 manufactured by Daicel Chemical Industries, Ltd.); one (e.g., CELLOXIDE 2081 manufactured by Daicel Chemical Industries, Ltd.) in which 3,4-epoxycyclohexylmethanol and 3,4-epoxycyclohexane carboxylic acid are coupled with both ends of an ε-caprolactone oligomer through ester linkages as disclosed in each of JP 4-36263 A and JP 4-170411 A; and bis(3,4-epoxycyclohexylmethyl)adipate (e.g., ERL4299 manufactured by Union Carbide Corporation). Alternatively, epoxidized 3-cyclohexene-1,2-dicarboxylate bis-3-cyclohexenylmethyl ester and an ε-caprolactone adduct thereof (GT300 series such as "EPOLEAD GT301" manufactured by Daicel Chemical Industries, Ltd.) disclosed in JP 4-69360 A and JP 4-170411 A, and epoxidized butane tetracarboxylate tetraxis-3-cyclohexenylmethyl ester and an ε-caprolactone adduct thereof (GT400 series such as "EPOLEAD GT401" manufactured by Daicel Chemical Industries, Ltd.) are also commercially available as curable epoxy compounds each having a plurality of alicyclic epoxy groups. Cured products can be obtained by allowing such multifunctional epoxy compounds to react with various curing agents and curing catalysts. A cured product of an epoxy resin is allowed to have good heat-resistance, transparency, and dielectric properties that are characteristics of a resin prepared from a compound with an alicyclic skeleton. Such an epoxy compound is useful as an ingredient to be included in coatings, adhesives, ink, and sealants, or as an intermediate to prepare any of other valuable compounds in a variety of end uses including pharmaceutical agents and medical supplies.

CELLOXIDE 3000 has a methyl group on a carbon atom in the epoxy group so that the reactivity thereof is low due to its steric hindrance. Alternatively, since CELLOXIDE 2021, CELLOXIDE 2081, or ERL4299 has an ester group in the molecule, it has hydrolyzability. If they are used under high temperatures and high moistures or under such a condition that a strong acid occurs, cured products thereof may suffer from decrease in physical properties.

Thus, a multifunctional epoxy compound with an alicyclic skeleton having no ester group in the molecule has been desired.

The Russian literature (Neftekhimiya, 1972, 12, 353.) discloses dicyclohexyl-3,3'-diepoxide as the representative of alicyclic diepoxy compounds represented by the general formula (I) described below. In the literature, peroxydate (where the peroxydate refers to t-butylhydroperoxide) as an epoxidizing agent and molybdenum chloride (V) in a catalytic amount are utilized for synthesis. In this literature, the peroxydate is used at high temperatures above 80° C. or more. Therefore, as the risk that the peroxydate is explosively decomposed is involved, there is a problem in safeness. In addition, molybdenum chloride (V) used as a catalyst is expensive and strongly poisonous. Therefore, a preparation process that is economical and gives environmental consideration has been sought.

On the other hand, a cured product of an epoxy resin typically has excellent performance in mechanical properties, water resistance, corrosion resistance, adhesion, chemical resistance, heat resistance, electrical characteristics, and so on, and is therefore utilized in a wide range of fields such as adhesives, paintings, laminated boards, encapsulating materials for IC, and molding materials.

Of those, for example, aromatic epoxy resins for general purposes, a glycidyl ether-based epoxy resin typified by a bisphenol-based epoxy resin, a phenol novolak-based epoxy resin, or the like, is used as a cured product to be cured under various curing conditions by the addition of a curing agent and optionally a curing accelerator, and, if necessary, the addition of a filler such as talc, titanium, or silica.

However, the cured product composed of the above aromatic epoxy resin for general purpose that is a glycidyl ether-based epoxy resin has the structure of an aromatic nucleus, so it has inferior weatherability outdoors. Additionally, when the viscosity of the glycidyl ether-based epoxy resin described above is measured at 25° C. using an E-type rotation viscometer (e.g., one manufactured by Tokyo Keiki Co.), the glycidyl ether-based epoxy resin typically has low fluidity, for example, 4,000-20,000 mPa·s for a bisphenol A type and 1,500-4,500 mPa·s for a bisphenol F type. Therefore, the glycidyl ether-based epoxy resin is mostly used by being dissolved in a solvent typified by toluene, xylene, methyl ethyl ketone, ethyl acetate, or the like, which causes a problem with workability and environmental safeness.

Known examples of an epoxy resin that has sufficiently low viscosity even if no diluent is used include one having a cyclohexene oxide skeleton (alicyclic skeleton). An epoxy compound having an alicyclic skeleton is characterized by having the same degree of reactivity as that of a glycidyl ether-based epoxy compound and is currently commercially available in various types. Examples of a monofunctional epoxy compound with an alicyclic skeleton in the molecule include monoepoxidized 4-vinylcyclohexene. Examples of a bifunctional epoxy compound include 4-vinylcyclohexene diepoxide and limonene diepoxide, and the like.

Such the compound having an alicyclic skeleton is free of halogens because no halide is used in its preparation process, and thus has superior electrical characteristics. Moreover, the compound is allowed to have heat resistance and transparency that are characteristics of a resin using a compound with an alicyclic skeleton.

Such the epoxy compound with an alicyclic skeleton and a resin composition containing it are used in the ingredients of coatings, adhesives, ink, and sealants, or stabilizers for various thermoplastic resins, or in a variety of end uses including pharmaceutical agents and medical supplies. In addition, it is known that the epoxy compound and the resin composition are useful also as intermediates for preparing other valuable compounds.

Since the epoxy compound with an alicyclic skeleton has sufficient performance but slightly lower reactivity when used in the above applications, the cured product thereof may suffer from decrease in physical properties and reactivity. Thus, a highly reactive alicyclic epoxy compound has been desired. Furthermore, the foregoing monoepoxidized 4-vinylcyclohexene and limonene diepoxide evaporate at room temperature, which causes a problem with working surroundings.

Alternatively, one example of an alicyclic diepoxy compound similar to alicyclic diepoxy compounds represented by the general formula (I) according to the present invention described below is an alicyclic diepoxy compound in which two alicyclic structures are connected by a methylene group or the like (e.g., JP 58-172387 A and JP 50-10636 B).

Additionally, in recent years, a curable resin composition obtained by blending or modifying an oxetane compound, a cationic polymerization initiator, and an alicyclic diepoxy compound has been proposed (e.g., JP2002-53659 A and JP2002-82527A). However, none of those curable resin compositions each including the alicyclic diepoxy compound has displayed satisfactory performance yet.

The inventors of the present invention have found that a curable epoxy resin composition containing: an alicyclic diepoxy compound represented by the general formula (I) described hereinafter; and an initiator for thermal cationic or photocationic polymerization, or an acid anhydride, and a cured product obtained by curing the composition have excellent properties.

Conventionally, electronic parts such as diodes, transistors, and integrated circuits are encapsulated with thermocuring resins. Specifically, in an integrated circuit, systems each composed of an o-cresol novolak-based epoxy resin or biphenyl-based epoxy resin system and a novolak-based phenol resin that have excellent heat resistance and moisture resistance are mostly used.

In pursuit of miniaturization, weight reduction, and enhanced performance of recent electronic equipments, along with the integration of semiconductors, a conventional through-hole mounting manner where a lead pin is inserted into a hole of a substrate is being replaced with a surface mounting manner where components are soldered to the surface of a substrate. In the surface mounting manner, unlike the through-hole mounting manner, the entire package sealed with an encapsulating resin is heated at high temperatures of 210 to 270° C. at the time of soldering during the mounting process. Therefore, cracks occur in the portion of the resin and cracks and exfoliation occur around a chip, which reduces reliability, resulting in a problem of unusability as a product.

Although many hypotheses are put forward regarding the mechanism of the emergence of cracks, the mechanism is generally considered as follows: during the mounting process, the encapsulating resin for a package absorbs moisture; on the other hand, in the surface mounting operation, the entire package is exposed under high temperatures above 200° C., and, in the case of a thin package, the temperature within the package exceeds 200° C. in a short period of time; if the package absorbing moisture is rapidly heated above 200° C., an internal pressure is generated by the vaporization of the moisture; when the internal pressure of the package exceeds the rapture strength of encapsulating materials, cracks occur.

Moreover, boundary separation may be attributed to the contraction in volume that take places during the curing of a curable resin such as an epoxy resin, or to the thermal stress within the package that is generated by the difference of the coefficients of linear expansion between a metal and a molding material for the epoxy resin.

In order to overcome the above disadvantages, a method of increasing the elasticity of the resin for encapsulation or decreasing the coefficient of liner expansion has been employed. One example is a method for higher loading of a filler. Although higher loading of a filler is effective means, it has limitations and may cause increase in viscosity and decrease in fluidity of the resin for encapsulation. The increased viscosity of the resin for encapsulation results in the deformation and cutting of a lead wire and the decreased fluidity results in lower loading, which may reduce reliability.

A variety of multifunctional epoxy compounds each having an alicyclic skeleton in the molecule have been known as resins for the encapsulation of electronic parts.

However, as described above, 1,2,8,9-diepoxylimonene has a methyl group in carbon constituting an epoxy group and thus the epoxy group has low reactivity compared to one having no methyl group. In addition, 3,4-epoxycyclohexylmethyl 3',4'-epoxycyclohexane carboxylate, bis(3,4-epoxycyclohexylmethyl)adipate and a lactone adduct thereof, and epoxidized butanetetracarboxylic acid tetraxis-3-cyclohexenylmethyl ester and an ε-caprolactone adduct thereof each have an ester group in the molecule so that hydrolysis may be generated.

Therefore, as described above, the physical properties of the cured product may be lowered owing to the use under high temperatures and high moisture and to hydrolysis.

In addition, as described above, an alicyclic epoxy compound in which two alicyclic structures are connected by a methylene group or the like has been known as an alicyclic epoxy compound similar to the alicyclic epoxy compound (a) represented by the above formula (I) (e.g., JP 2002-275169 A, JP 58-172387 A, and JP 50-10636 B). However, the epoxidation rate of the epoxy compound is somewhat low.

In addition, JP 2001-181481 A discloses an epoxy resin composition for the encapsulation of semiconductors utilizing a biphenyl-based epoxy resin, which has superior water-absorbing properties but still has a problem with fluidity and torque in curing, that is, moldability.

Thus, it is desired to develop a highly flowable epoxy compound having another alicyclic skeleton without an ester group in the molecule. The inventors of the present invention have found that an epoxy resin composition containing: the alicyclic epoxy compound (a) represented by the general formula (I) described below; and a curing agent has excellent properties as a resin composition for the encapsulation of electronic parts.

In an application for an electrical insulating oil, an electrical insulating oil for oil-immersed transformers, specifically open-type transformers, in which the insulating oil contacts air, must be excellent in oxidation stability. Thus, one containing an antioxidant, particularly a phenolic antioxidant is studied (JP 9-272891 A). However, for example, an electrical insulating oil (JP 2002-260445 A) supplemented with 0.3% by weight of DBPC (2,6-di-tert-butyl-p-cresol) shows that a total acid value already rises (0.02-0.03 mg KOH/g) through the phenomenon of oxidation at 120° C.×75 hours in the oxidation stability test of JIS C 2101-1993. That is, it is thought that the induction period of oxidation terminates in 75 hours and then a rise in total acid value proceeds abruptly.

On the other hand, as a technique for using an epoxy compound as a stabilizer for an electrical insulating oil to entrap impurities in the component of the insulating oil and to disperse discharge energy, an insulating oil for capacitors has been disclosed in JP 3-171510 A and JP 7-226332 A. However, the epoxy compound utilized is mainly an alicyclic diepoxy compound or an aromatic diepoxy compound having, in the molecule, an ester linkage or an ether linkage which generates hydrolysis and pyrolysis in the long-term use and may not occasionally show an antioxidant function as a result. Moreover, in general, since a capacitor has the sealed structure in which an insulating oil is enclosed, it is deformed by gas generated from decomposition or made unusable owing to the reduction in breakdown voltage and capacitance.

On the other hand, in an insulating portion of electric equipment, a connecting portion of a power cable, and the like, a cast article of an epoxy resin composition embedded with a metal electrode is arranged so as to support a conductor in the portion of the above metal electrode. In general, such a cast article of the epoxy resin composition is produced using an epoxy resin composition composed of a multifunctional epoxy resin, an acid anhydride, a filler, and so on. In particular, a bisphenol-based epoxy resin as the epoxy resin, phthalic anhydride as the acid anhydride, and inorganic powder such as alumina or silica as the inorganic filler are used. Crack resistance, mechanical strength, and electric properties have been balancedly improved by using them.

Recently, the tendency for the miniaturization in size and ultra high-voltage of a high-voltage instrument is intensifying more and more. The cast article of the epoxy resin composition having further sophisticated performance is required. Thus, a conventional cast article of an epoxy resin composition has limitations on electric properties and mechanical properties and potentially leads to breakdown. That is, along with a shift to an ultra high-voltage, an insulator (using the casting epoxy resin composition for electrical insulation) is subjected to a high electric field. Therefore, the insulator is required to further improve withstand voltage strength. Moreover, since dielectric loss ($\epsilon.\tan \delta.E2$) is enlarged along with an ultra high-voltage, the thermal damage of an insulator may be caused by the generated heat. Specifically, if $\epsilon.\tan \delta$ increases with increasing temperature, the breakdown by thermal runaway cannot be denied. Additionally, the adhesiveness with a metal electrode embedded in an insulator and the crack resistance must be further improved.

For example, as disclosed in JP 9-77847 A, by using a bisphenol A-based epoxy resin and a novolak epoxy resin as epoxy resins, a resin for insulation is made by mixing two or more acid anhydrides. Similarly, JP 11-60908 A illustrates that a resin for insulation is made by mixing a bisphenol A-based epoxide and a crystalline epoxide as epoxy resins with two or more acid anhydrides.

Those compositions are not suitable for casting and impregnation because the compositions are of solid.

DISCLOSURE OF THE INVENTION

An object of the present invention (1) is to provide a process for preparation of a less viscous and easily manageable alicyclic diepoxy compound without an ester group in the molecule, which has improved safeness, is economical, and gives environmental consideration.

In addition, an object of the present invention (2) is to provide a curable resin composition having the alicyclic diepoxy compound, an initiator for thermal cationic or photocationic polymerization, or an acid anhydride as essential ingredients and to provide a cured product obtained by hardening the composition, which has higher performance in reactivity to curing as well as in transparency, heat resistance, processibility, safeness in working, and so on, than that of an epoxy compound (resin) conventionally utilized.

Moreover, an object of the present invention (3) is to provide an epoxy resin composition for the encapsulation of electronic parts having high fluidity, good loading properties, and excellent moisture resistance in which the above problems of a resin for encapsulating electronic parts are overcome by blending the alicyclic diepoxy compound represented by the general formula (I) described below. In such an epoxy resin composition, when parts having an electronic circuit such as a semiconductor device are encapsulated, no lead wire is deformed or cut.

Furthermore, an object of the present invention (4) is to provide a stabilizer for an electrical insulating oil having more excellent oxidation stability in long-term use than conventional one and to provide an electrical insulating oil which has been stabilized.

Additionally, an object of the present invention (5) is to provide a cured product having excellent heat resistance, electrical characteristics, and mechanical properties, which is obtained by defining, within a certain range, the blending ratio of an epoxy resin composition containing the alicyclic diepoxy compound represented by the general formula (I) described below, an acid anhydride, a curing accelerator, and an inorganic filler without loss of the casting workability of a casting epoxy resin composition for electrical insulation.

According to the present invention (5), the casting epoxy resin composition for electrical insulation which is superior in both electrical characteristics and mechanical properties can be obtained, specifically by using fused alumina as the above inorganic filler. In particular, it is revealed that withstand voltage characteristics can be improved by 30-50% compared to the case where an electrically fused alumina is used.

The inventors of the present invention have conducted an extensive study for attaining the above objects and have found that: a highly pure diepoxy compound can be economically obtained by using an organic percarboxylic acid in high yield; a resin composition containing such a diepoxy compound is less viscous, highly workable, and highly curable; a cured product obtained has excellent heat resistance and electrical characteristics; and further the diepoxy compound is useful as a stabilizer for an electrical insulating oil. The present inventions (1) to (5) have been completed based on this finding.

That is, a first aspect of the present invention provides a process for preparation of an alicyclic diepoxy compound represented by a general formula (I):

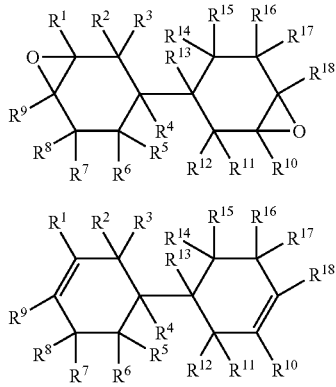

(wherein, each of $R^1$ to $R^{18}$, which may be the same or different, represents a hydrogen atom, a halogen atom, a hydrocarbon group that may contain an oxygen atom or a halogen atom, or an alkoxy group that may have a substitutional group), characterized by including:

epoxidizing an alicyclic diolefin compound represented by a general formula (II) described above with an organic percarboxylic acid.

A second aspect of the present invention provides a process for preparation of an alicyclic diepoxy compound according to the first aspect of the present invention, in which the organic percarboxylic acid is obtained by oxidation of a corresponding aldehyde with oxygen, and the organic percarboxylic acid contains substantially no water.

A third aspect of the present invention provides a process for preparation of an alicyclic diepoxy compound according to the first or second aspect of the present invention, in which a water content of the organic percarboxylic acid is 0.8% by weight or less.

A fourth aspect of the present invention provides a process for preparation of an alicyclic diepoxy compound according to the first aspect of the present invention, in which the organic percarboxylic acid is peracetic acid.

A fifth aspect of the present invention provides a process for preparation of an alicyclic diepoxy compound according to the fourth aspect of the present invention, in which the peracetic acid is an ethyl acetate solution.

In addition, a sixth aspect of the present invention provides a curable epoxy resin composition, characterized by including:

an alicyclic diepoxy compound (A) represented by the following general formula (I):

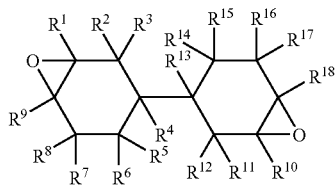

(wherein, each of $R^1$ to $R^{18}$, which may be the same or different, represents a hydrogen atom, a halogen atom, a hydrocarbon group that may contain an oxygen atom or a halogen atom, or an alkoxy group that may have a substitutional group);

a thermal cationic (b1) or photocationic (b2) polymerization initiator (B) or an acid anhydride (C); and an additional epoxy resin(D) which may be added optionally.

A seventh aspect of the present invention provides a curable epoxy resin composition according to the sixth aspect of the present invention, in which the alicyclic diepoxy compound represented by the general formula (I) is bicyclohexyl-3,3'-diepoxide.

An eighth aspect of the present invention provides a curable epoxy resin composition according to the sixth or seventh aspect of the present invention, in which the photocationic polymerization initiator is a sulfonium salt-based photocationic polymerization initiator.

A ninth aspect of the present invention provides a curable epoxy resin composition according to the sixth or seventh aspect of the present invention, in which the acid anhydride is methylhexahydrophthalic anhydride.

A tenth aspect of the present invention provides a cured product obtained by curing the curable epoxy resin composition according to any one of the sixth to ninth aspects of the present invention.

In addition, an eleventh aspect of the present invention provides an epoxy resin composition for encapsulation of electronic parts, including:

an alicyclic diepoxy compound (a) represented by the following general formula (I):

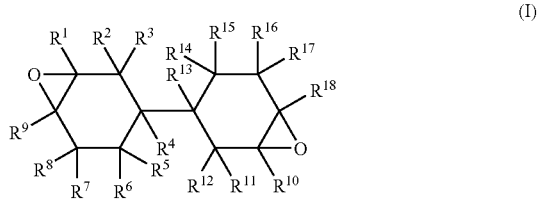

(wherein, each of $R^1$ to $R^{18}$, which may be the same or different, represents a hydrogen atom, a halogen atom, a hydrocarbon group that may contain an oxygen atom or a halogen atom, or an alkoxy group that may have a substitutional group);

a curing agent (b);

a curing accelerator (c);

an inorganic filler (d); and an additional epoxy resin (e), in which the (a) and (b) are essential ingredients, while the (c), (d), and (e) are optional ingredients.

A twelfth aspect of the present invention provides an epoxy resin composition for encapsulation of an electric component according to the eleventh aspect of the present invention, in which the alicyclic diepoxy compound (a) is bicyclohexyl-3,3'-diepoxide.

A thirteenth aspect of the present invention provides an epoxy resin composition for encapsulation of electronic parts according to the eleventh or twelfth aspect of the present invention, in which the curing agent (b) is at least one selected from an amine-based curing agent, an acid anhydride-based curing agent, and a phenol-based resin.

A fourteenth aspect of the present invention provides an epoxy resin composition for encapsulation of electronic parts according to the eleventh aspect of the present invention, in which the additional epoxy resin (e) is a cresol novolak-based epoxy resin.

A fifteenth aspect of the present invention provides a cured product obtained by curing the epoxy resin composition for encapsulation of electronic parts according to any one of the eleventh to fourteenth aspects of the present invention.

In addition, a sixteenth aspect of the present invention provides a stabilizer for an electrical insulating oil, including an alicyclic diepoxy compound represented by a general formula (I):

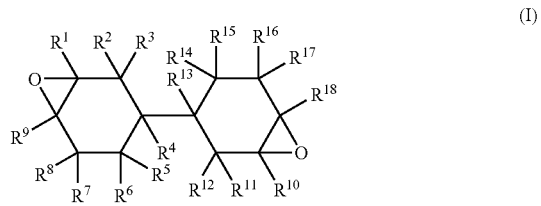

(I)

(wherein, each of $R^1$ to $R^{18}$, which may be the same or different, represents a hydrogen atom, a halogen atom, a hydrocarbon group that may contain an oxygen atom or a halogen atom, or an alkoxy group that may have a substitutional group).

An seventeenth aspect of the present invention provides a stabilizer for an electrical insulating oil according to the sixteenth aspect of the present invention, in which $R^1$ to $R^{18}$ in the alicyclic diepoxy compound represented by the general formula (I) are all hydrogen atoms.

An eighteenth aspect of the present invention provides a stabilizer for an electrical insulating oil according to the sixteenth or seventeenth aspect of the present invention, in which the alicyclic diepoxy compound represented by the general formula (I) is obtained by epoxidization of a corresponding diolefin compound with an organic percarboxylic acid that contains substantially no water.

A nineteenth aspect of the present invention provides a stabilizer for an electrical insulating oil according to the eighteenth aspect of the present invention, in which a water content of the organic percarboxylic acid is 0.8% by weight or less.

A twentieth aspect of the present invention provides a stabilizer for an electrical insulating oil according to the eighteenth or nineteenth aspect of the present invention, in which the organic percarboxylic acid is an organic solvent solution.

A twenty-first aspect of the present invention provides a stabilizer for an electrical insulating oil according to any one of the sixteenth to twentieth aspects of the present invention, in which the stabilizer is a stabilizer for an insulating oil used in a capacitor.

A twenty-second aspect of the present invention provides an electrical insulating oil characterized by being prepared by mixing 100 parts by weight of an insulating oil ingredient with 0.05 to 15 parts by weight of the stabilizer for an electrical insulating oil according to any one of the sixteenth to twenty-first aspects of the present invention.

In addition, a twenty-third aspect of the present invention provides a casting epoxy resin composition for electrical insulation, including a thermocuring resin and an inorganic filler, characterized in that:
the thermosetting resin includes:
(A) an epoxy resin composition composed of 5 to 80% by weight of an alicyclic diepoxy compound (a-1) represented by the following general formula (I):

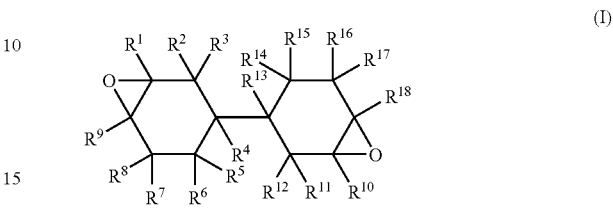

(I)

(wherein, each of $R^1$ to $R^{18}$, which may be the same or different, represents a hydrogen atom, a halogen atom, a hydrocarbon group that may contain an oxygen atom or a halogen atom, or an alkoxy group that may have a substitutional group), 95 to 20% by weight of an epoxy compound (a-2) other than the alicyclic diepoxy compound (a-1) represented by the formula (I) [total of the alicyclic diepoxy compound (a-1) and the epoxy compound (a-2) is 100% by weight];
(B) an acid anhydride; and
(C) a curing accelerator;

and the thermocuring resin further contains:
(D) the inorganic filler; and
a mixing ratio of the ingredient (B) is in a range of 0.6 to 1.0 equivalent based on 1 equivalent of the ingredient (A), a mixing ratio of the ingredient (C) is 0.5 to 10 parts by weight based on 100 parts weight of the (A) and (B) in total, and a mixing ratio of the ingredient (D) is 30 to 80% by weight of a total amount of the ingredients (A) to (D).

A twenty-fourth aspect of the present invention provides a casting epoxy resin composition for electrical insulation according to the twenty-third aspect of the present invention, in which the alicyclic diepoxy compound (a-1) represented by the general formula (I) is bicyclohexyl-3,3'-diepoxide.

A twenty-fifth aspect of the present invention provides a casting epoxy resin composition for electrical insulation according to the twenty-third aspect of the present invention, in which the acid anhydride is methylhexahydrophthalic anhydride or methyl norbornene dicarboxylic anhydride.

A twenty-sixth aspect of the present invention provides a casting epoxy resin composition for electrical insulation according to the twenty-third aspect of the present invention, in which the curing accelerator is ethylene glycol or diazabicycloundecene.

A twenty-seventh aspect of the present invention provides a casting epoxy resin composition for electrical insulation according to the twenty-third aspect of the present invention, in which the inorganic filler is a spherical fused silica or fused alumina.

A twenty-eighth aspect of the present invention provides a casting epoxy resin composition for electrical insulation according to the twenty-third aspect of the present invention, in which the epoxy compound (a-2) is at least one of 3,4-epoxycyclohexylmethyl-3,4-epoxy cyclohexane carboxylate, a bisphenol-based epoxy resin, and a novolak phenol-based epoxy resin.

A twenty-ninth aspect of the present invention provides a cured product obtained by curing the casting epoxy resin composition for electrical insulation according to any one of the twenty-third to twenty-eighth aspects of the present invention.

BEST MODE FOR CARRYING OUT THE INVENTION

Figure 1:
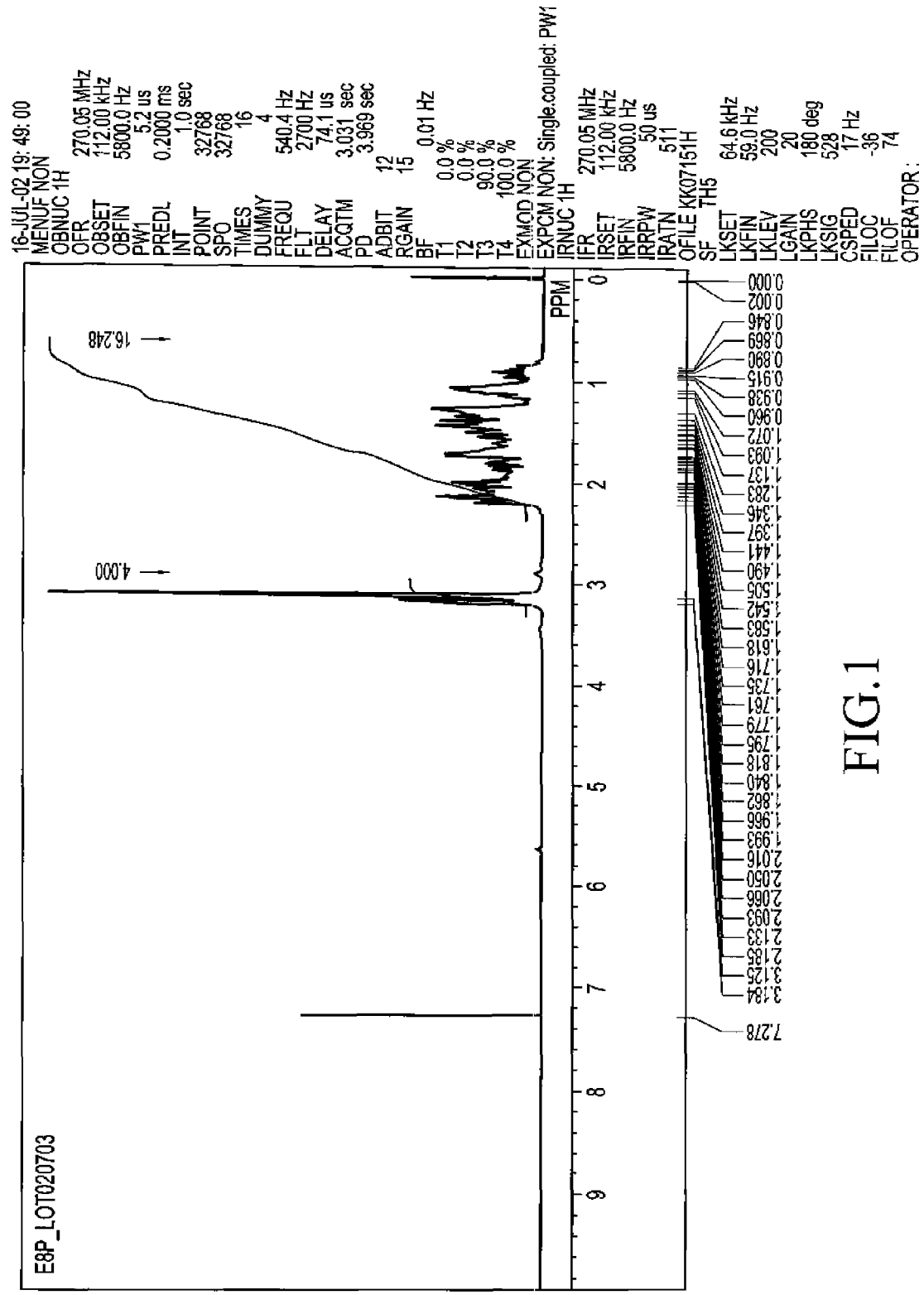
FIG. 1 shows an NMR chart of an alicyclic diepoxy compound obtained in Example 1.

Hereinafter, the present invention (1) will be described in detail.

An alicyclic diepoxy compound represented by the general formula (I) in the present invention (1) is prepared by oxidation of an unsaturated compound having a bicyclohexyl-3,3'-diene skeleton represented by the general formula (II) with an organic percarboxylic acid.

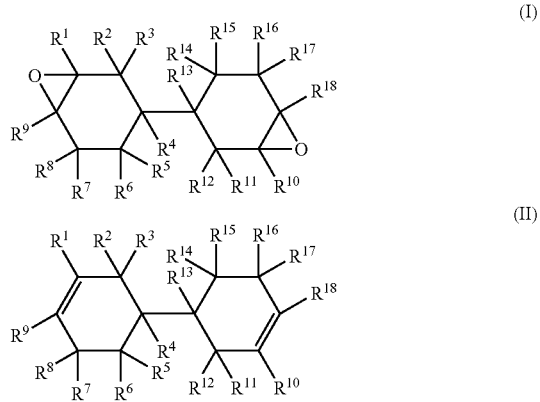

In the general formula (I) and the general formula (II), each of $R^1$ to $R^{18}$, which may be the same or different, represents a hydrogen atom, a halogen atom, a hydrocarbon group that may contain an oxygen atom or a halogen atom, or an alkoxy group that may have a substitutional group.

The above unsaturated compound having a bicyclohexyl-3,3'-diene skeleton is generally synthesized by dehydration of a compound with a hydroxyl group. A preparation process in which such an unsaturated compound is synthesized from a compound having a cyclohexanol structure is described in "Synthesis and Reaction of Organic Compounds (I)," pp. 114-127, *Shin-Jikken Kagaku Koza* 14 published by Maruzen Co., Ltd., JP 58-172387 A, JP 2000-169399 A, and so on.

According to the present invention (1), the alicyclic epoxy compound can be prepared by the reaction of an unsaturated compound having a bicyclohexyl-3,3'-diene skeleton with an organic percarboxylic acid.

In the preparation process of the present invention (1), the organic percarboxylic acid (the organic percarboxylic acid refers to performic acid, peracetic acid, perbenzoic acid, perisobutyric acid, trifluoroperacetic acid, etc.) can be used as an epoxidizing agent. Of the organic percarboxylic acids, specifically peracetic acid is a preferable epoxidizing agent because of its reactivity, as well as high stability, required for preparing the alicyclic epoxy compound in the present invention.

Of those, it is preferred to use an organic percarboxylic acid substantially containing no water, specifically with a water content of 0.8% by weight or less, preferably 0.6% by weight or less in order to obtain a compound having a high epoxidation rate. In the present invention (1), the organic percarboxylic acid substantially containing no water is prepared by the air oxidation of aldehydes, for example acetaldehyde. For instance, peracetic acid is prepared by a process as described in German Patent Application Publication No. 1418465 or JP54-3006A. According to this process, in comparison with a process of synthesizing an organic percarboxylic acid from hydrogen peroxide followed by extraction by a solvent to produce an organic percarboxylic acid, an organic percarboxylic acid having high concentration can be synthesized continuously in a large amount and can be therefore obtained at a substantially low price.

Although there is no strict limitation on the amount of the epoxidizing agent, the optimum amount in each case is determined depending on variable factors such as the reactivities of individual epoxidizing agents and alicyclic olefin compounds used, and the epoxidation rate of interest.

The epoxidation reaction is performed by adjusting the use or unuse of a solvent and reaction temperature in accordance with an apparatus and the physical properties of raw materials. A solvent can be used for the purposes of reducing the viscosity of raw materials, stabilizing the epoxidizing agent by dilution, and so on. Esters, aromatic compounds, ethers, and the like can be used in the case of peracetic acid. A specifically preferable solvent is ethyl acetate, hexane, cyclehexane, toluene, benzene, or the like. Of those solvents, ethyl acetate is specifically preferable. The reaction temperature is determined depending on the reactivity of an epoxidizing agent and an unsaturated group-containing compound utilized.

For example, if peracetic acid that is a preferable epoxidizing agent is used, the reaction temperature is preferred to be at 20 to 70° C. The reaction is slow at temperatures less than 20° C., and peracetic acid is decomposed with heat generation at temperatures beyond 70° C., which is not preferable.

The molar ratio for preparing the epoxidizing agent relative to unsaturated bond can be varied depending on how much unsaturated bond is desired to remain, and so on. If a compound having a high epoxidation rate is demanded, preferably 1.0 to 3.0 mol, more preferably 1.05 to 1.5 mol of the epoxidizing agent is added based on 1 mol of an unsaturated group. In general, the epoxidizing agent beyond 3.0-fold mol is disadvantageous in view of cost efficiency and side reaction. According to the preparation process of the present invention (1), there is no need to use any expensive epoxidizing agent or catalyst.

A crude solution obtained from the reaction does not require any specific manipulation. For example, the crude solution may be aged while agitating for 1 to 5 hours. Appropriate methods for isolation of the epoxy compound from the resultant crude solution include a method of precipitating the epoxy compound with a poor solvent, a method of putting the epoxy compound into hot water under agitation to remove the solvent by distillation, and a method of directly eliminating the solvent.

The alicyclic diepoxy compound represented by the above general formula (I), which is produced in the preparation process of the present invention (1), is able to produce various coatings, ink, adhesives, sealants, or molded products, or an intermediate for other applications using such an alicyclic diepoxy compound, through single polymerization or copolymerization, or by further reacting with other compounds. Examples of the end uses employing the alicyclic diepoxy compound represented by the above general formula (I) include: agents for removing oxygen; coatings for furnitures; decorative coatings; coatings for beverage cans and the other cans; adhesives; under coatings for automobiles; sealers; finishings; inks for textual information or image information; sealants for electronic parts; photoresists suitable for developing printing plates or printed circuit boards; casting rolls for printing; glass composed mainly of unsaturated polyester and styrene; moldings of molding blends or sheet-forming blends reinforced with carbon, graphite, or other fibers; solvents; flame retardants; and intermediates to prepare other valuable compounds in various end uses including pharmaceutical products and medical supplies.

In addition, the alicyclic diepoxy compound represented by the above general formula (1) is allowed to have heat-resistance, transparency, and good dielectric properties that are characteristics of a resin using a compound having an alicyclic skeleton.

Hereinafter, the present invention (2) will be described in detail.

The present invention (2) relates to a curable epoxy resin composition having, as an essential ingredient, a diepoxy compound having an alicyclic skeleton but no ester linkage, and also relates to a cured product thereof.

The alicyclic diepoxy compound (A), which is an essential resin ingredient in the curable epoxy resin composition of the present invention (2), represented by the following general formula (I):

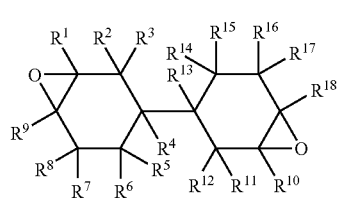

(wherein, each of $R^1$ to $R^{16}$, which may be the same or different, represents a hydrogen atom, a halogen atom, a hydrocarbon group that may contain an oxygen atom or a halogen atom, or an alkoxy group that may have a substitutional group) is generally known and can be prepared using, for example, the preparation process of the present invention (1) or a process described in JP Application Specification 2002-260490 or the Russian literature (Neftekhimiya, 1972, 12, 353). In particular, as described in the preparation process of the present invention (1), one prepared by the epoxidation of a corresponding diolefin compound with an organic percarboxylic acid that has low water content is preferable because of its high content of the diepoxy compound. Bicyclohexyl-3,3'-diepoxide where all of $R^1$ to $R^{18}$ are a hydrogen atom is preferably used as a specific example of the alicyclic diepoxy compound (A) represented by the above general formula (I).

The curable epoxy resin composition of the present invention (2) contains, as an essential ingredient, a curing agent (B) in addition to the alicyclic diepoxy compound (A) represented by the above general formula (I), and may further contain another epoxy resin (D), a curing accelerator, and an additional filler or additive.

As the curing agent (B), it is essential to use a cationic polymerization initiator or an acid anhydride (C) which generates cationic species through light or heat. Having a photocationic polymerization initiator (b1) or a thermal cationic polymerization initiator (b2), or an acid anhydride (C) as the essential ingredient of the curing agent (B), the curable epoxy resin composition of the present invention (2) can be curably polymerized through light or heat.

Any one of sulfonium salt based-, iodonium salt based-, diazonium salt based-, allene-ion complex based-compounds, and the like can be used as the photocationic polymerization initiator (b1). Examples thereof include: UVA-CURE1590 and UVACURE1591 (manufactured by Daicel UCB Co., Ltd.), DAICAT11 (manufactured by Daicel Chemical Industries, Ltd.), CD-1011 (manufactured by Sartomer Co.), SI-60L, SI-80L, and SI-100L (manufactured by Sanshin Chemical Industries, Ltd.), etc., of a sulfonium salt based-compound; DAICAT12 (manufactured by Daicel Chemical Industries, Ltd.) and CD-1012 (manufactured by Sartomer Co.) of an iodonium salt based-compound; and SP-150 and SP-170 (manufactured by Asahi Denka Co., Ltd.) of a diazonium salt based-compound. Of the photocationic polymerization initiators, SI-60L, SI-80L, and SI-100L described above can generate cations also by heating.

In addition, a silanol-based cationic catalyst such as triphenylsilanol or an aluminum chelate-based catalyst such as aluminum tris(acetylacetone) can be also used as the thermal cationic polymerization initiator (b2).

In the present invention (2), it is suitable to blend the above cationic polymerization initiator on the order of 0.01 to 20 parts by weight, preferably 0.1 to 5 parts by weight, more preferably 0.1 to 3 parts by weight, with respect to 100 parts by weight of the total amount of the alicyclic diepoxy compound represented by the general formula (1) and another epoxy resin added optionally which is described below. Blending 0.01 parts by weight or less of the initiator significantly reduces thermal curability, which is not preferable. Blending the initiator beyond 20 parts by weight is uneconomical because it shows no weighting effect, and results in reduction in the physical properties of the cured product, which is not preferable.

Additionally, in the present invention (2), an acid anhydride (C) can be also used as the curing agent. The acid anhydride is preferred to be an anhydride with a carbon number of 4 to 25, preferably 8 to 20 having one or two aliphatic rings, or one or two aromatic rings as well as one or two acid anhydride groups in the molecule such as phthalic anhydride, maleic anhydride, trimellitic anhydride, tetrahydrophthalic anhydride, methyltetrahydrophthalic anhydride, methylnorbornenedicarboxylic anhydride, methylhexahydrophthalic anhydride, hexahydrophthalic anhydride, methylhimic anhydride, pyromellitic dianhydride, benzophenonetetracarboxylic dianhydride, 3,3',4,4'-biphenyltetracarboxylic dianhydride, bis(3,4-dicarboxyphenyl)ether dianhydride, bis(3,4-dicarboxy phenyl)methane dianhydride, or 2,2'-bis(3,4-dicarboxyphenyl)propane dianhydride.

Each of the acid anhydrides is used alone or two or more of them is used in combination. Of those, methylhexahydrophthalic anhydride and, tetrahydrophthalic anhydride, and the like are preferably used because they give excellent heat resistance and further improved electrical characteristics and mechanical strength.

In this case, one in which the content of a compound having a carboxyl group (COOH group) is 0.5% by weight or less (i.e., 0 to 0.5% by weight), specifically 0.4% by weight or less (i.e., 0 to 0.4% by weight) is used as the acid anhydride. If the content of a carboxyl group is above 0.5% by weight, undesirable crystallization may occur. In this case, one having a content of a carboxyl group (COOH group) of 0.3% by weight or less (i.e., 0 to 0.3% by weight), specifically 0.25% by weight or less (i.e., 0 to 0.25% by weight) for the curing agent of acid anhydride is preferable for the same reason.

It is preferred that as the blending quantity of an acid anhydride, the ratio of an acid anhydride group be in the range of 0.3 to 0.7 mol based on 1 mol of the total amount of an epoxy group in the alicyclic diepoxy compound represented by the general formula (I) and another epoxy resin added optionally, which is described below. If the ratio is less than 0.3 mol, curability is insufficient. If the ratio is above 0.7 mol, an unreacted acid anhydride may remain, which causes reduction in the glass-transition temperature. More preferably, the ratio is in the range of 0.4 to 0.6 mol.

Additionally, examples of the curing accelerator, which can be used for curing, include, but is not limited to: an amidine compound such as 1,8-diazabicyclo(5,4,0)undecene (DBU); an organic phosphorous compound such as triphenylphosphine, tetraphenyl phosphonium, or tetraphenylborate; and an imidazole compound such as 2-methylimidazole. Such a curing accelerator can be used alone or mixed with another one. It is preferred that the blending quantity be in the range of 0.4 to 20 parts by weight based on 100 parts by weight of the total amount of the alicyclic diepoxy compound represented by the above general formula (I), another epoxy resin added optionally which is described below, and the polymerization initiator. If the blending quantity is less than 0.4 part by weight, sufficient curability may not be obtained in thermally molding. On the other hand, if the blending quantity is beyond 20 parts by weight, it is anxious that the curing is so fast that undesirable failure in loading may occur owing to lower fluidity in molding.

Another epoxy resin added optionally to the alicyclic diepoxy compound represented by the general formula (I) in the present invention (2) is not particularly limited. Examples thereof include a bisphenol A-based epoxy resin, a bisphenol F-based epoxy resin, a bisphenol S-based epoxy resin, a bisphenol AD-based epoxy resin, a naphthalene-based epoxy resin, a biphenyl-based epoxy resin, and a bifunctional epoxy resin selected from halides thereof.

In addition to the above, examples thereof include: novolak epoxy resins such as phenol novolak epoxy resins, bromophenol novolak epoxy resins, orthocresol novolak epoxy resins, bisphenol A novolak epoxy resins, and bisphenol AD novolak epoxy resins; alicyclic epoxy resins such as epoxy resins having tricyclodecene oxide groups and dicyclo pentanediene-based phenol resins; aromatic epoxy resins such as naphthalene-based phenol resins; glycidylester epoxy resins such as dimer acid glycidylester and triglycidylester; glycidylamine epoxy resins such as tetraglycidylamino diphenylmethane, triglycidyl p-aminophenol, triglycidyl-p-aminophenol, tetraglycidyl methaxylylene diamine, and tertaglycidyl bisamino methylcyclohexane; heterocyclic epoxy resins such as triglycidyl isocyanurate; trifunctional epoxy resins such as phloroglycinol triglycidylether, trihydroxybiphenyl triglycidylether, trihydroxyphenylmethane triglycidylether, glycerin triglycidylether, 2-[4-(2,3-epoxypropoxy)phenyl]-2-[4-[1,1-bis[4-(2,3-epoxypropoxy)phenyl]ethyl]phenyl]propane, and 1,3-bis[4-[1-[4-(2,3-epoxypropoxy)phenyl]-1-[4-[1-[4-(2,3-epoxypropoxy)phenyl]1-methylethyl]phenyl]ethyl]phenoxy]-2-propanol; tetrafunctional epoxy resins such as tetrahydroxy phenylethane tetraglycidylether, tetraglycidyl benzophenone, bisresorcinol tetraglycidylether, and tetraglycidoxy biphenyl; and alicyclic epoxy resins such as 3,4-epoxy cyclohexenylmethyl-3',4'-epoxy cyclohexenyl carboxylate (Celloxide 2021 available from Daicel Chemical Industries, Ltd.), limonene diepoxide (Celloxide 3000 available from Daicel Chemical Industries, Ltd.), ε-caprolactone modified 3,4-epoxy cyclohexenylmethyl-3',4'-epoxy cyclohexenyl carboxylate (Celloxide 2081 available from Daicel Chemical Industries, Ltd.), bis(3,4-epoxy cyclohexenylmethyl)adipate (including ERL4299 available from Union Carbide Corporation), epoxidized 3-cyclohexene-1,2-dicarboxylic acid bis 3-cyclohexenylmethylester, and ε-caprolactone adducts thereof (GT300 series including "Epolead GT301" available from Daicel Chemical Industries, Ltd.), and epoxidized butane tetracarboxylic acid tetraxis-3-cyclohexenylmethylester and ε-caprolactone adducts thereof (GT400 series including "Epolead GT401" available from Daicel Chemical Industries, Ltd.). The addition amount of another epoxy resin, which is optionally added, is 1 to 10,000 parts by weight, preferably 100 to 8,000 parts by weight, more preferably 1,000 to 5,000 parts by weight based on 100 parts by weight of the alicyclic diepoxy compound represented by the general formula (I). When the amount is less than 1 part by weight, it is no meaning to add another epoxy resin which is optionally added. Otherwise, when the addition amount is more than 10,000 parts by weight, the excellent properties by the alicyclic diepoxy compound represented by the general formula (I) do not appear in the cured product.

Further, the curable epoxy resin composition of the present invention (2), if necessary, may contain a thermoplastic resin such as a polyethylene, a polypropylene, a polystyrene, a polyethylene terephthalate, a polycaprolactone, a polycarbonate, or a polyarylate.

The curable epoxy resin composition of the present invention (2) may also contain synthetic rubbers and elastomers such as a polybutadiene and a polybutadiene polystyrene copolymer. The curable epoxy resin composition of the present invention (2) may contain polyamide resins such as a 6,6-nylon and nitrogen-containing compounds such as polyimide resins.

The curable epoxy resin composition of the present invention (2) may also contain a phenol resin. Examples thereof include novolak epoxy resins, dicyclopentadiene copolymer novolak phenol resins, naphthalene copolymer novolak phenol resins, biphenyl copolymer novolak phenol resins, xylene copolymer novolak phenol resins, cresol novolak phenol resins, dicyclopentadiene copolymer cresol novolak phenol resins, naphthalene copolymer cresol novolak phenol resins, biphenyl copolymer cresol novolak phenol resins, naphthalene copolymer cresol novolak phenol resins, resol phenol resins, dicyclopentadiene copolymer resol resins, naphthalene copolymer resol resins, biphenyl copolymer resol resins, and xylene copolymer resol resins.

The addition amount of the polyethylene and the like, and phenol resins added optionally is 1 to 10,000 parts by weight, preferably 100 to 8,000 parts by weight, more preferably 1,000 to 5,000 parts by weight based on 100 parts by weight of the alicyclic diepoxy compound represented by the general formula (I). If the amount is less than 1 part by weight, there is no point of adding the polyethylene and the like. In contrast, if the amount is above 10,000 parts by weight, excellent properties by the alicyclic diepoxy compound represented by the general formula (I) do not appear in cured products.

In the curable epoxy resin composition of the present invention (2), the filler can be optionally used. Although each of organic and inorganic fillers can be used as a filler, the inorganic filler is preferable, taking a coefficient of thermal expansion into consideration.

Examples of the organic fillers include: nitrogen atom-containing thermoplastic resins such as acrylic resins; thermoplastic resins such as polystyrene resins, polyethylene resins, epoxy resins, and silicone resins; and thermoplastic elastomers. Examples of the inorganic fillers include alumina, talc, glass powders, ceramic powders, crystalline silica, and fused silica. Further, the content of the filler is not particularly limited as long as it does not influence the effect of the present invention (2).

Further, examples of the additive to be used in the present invention (2) include: stress-reducible agents such as nitrogen atom-containing thermosetting resins and organic synthetic rubbers; waxes such as carnauba waxes, higher fatty acids, and synthetic waxes; coloring agents such as carbon black; halogen trap agents; leveling agents; and curing accelerators.

In order to mix each of the above ingredients, after sufficient mixing with an apparatus ordinarily used, for example, a mixer such as a blender, and further melt-kneading with a heat roll, a kneader, and so on, followed by cooling, the resultant mixture is pulverized to form a molding material. Additionally, for encapsulating electronic parts such as a semiconductor element to produce a semiconductor device, the encapsulation is performed by a molding method such as transfer molding, compression molding, or injection molding.

The curable epoxy resin composition of the present invention (2) is cured at temperatures of 30 to 240° C., preferably 35 to 180° C., more preferably 35 to 60° C. and for a curing time of 30 to 300 minutes, preferably 45 to 240 minutes, more preferably 60 to 120 minutes.

If the curing temperature and curing time are under the lower limits of the above-mentioned ranges, the curing is insufficient. In contrast, when they are above the upper limits of the above-mentioned ranges, the decomposition of the resin ingredients may occur. Thus, each of cases is undesirable. The curing condition, which depends on various conditions, can be adjusted appropriately so that the curing time is shorter in the case of higher curing temperatures, and the curing time is longer in the case of lower curing temperatures. Typically, following a primary curing (curing temperature: 30 to 240° C., preferably 35 to 180° C., more preferably 35 to 60° C.; curing time: 30 to 300 minutes, preferably 45 to 240 minutes, more preferably 60 to 120 minutes), a secondary curing (curing temperature: 60 to 240° C., preferably 90 to 200° C., more preferably 120 to 200° C.; curing time: 30 to 180 minutes, preferably 45 to 150 minutes, more preferably 60 to 120 minutes) is performed so as not to cause insufficient curing.

The curable epoxy resin composition can be cured by irradiation with light such as ultraviolet rays or active energy beam, for example, electron beam.

For example, a high-pressure mercury lamp, a super high-pressure mercury lamp, a carbon arc lamp, a xenon lamp, a metal halide lamp, or the like is utilized as a light source in performing ultraviolet irradiation. Although an irradiation time differs depending on a type of the light source, a distance between the light source and the applied surface, and other conditions, it is several tens of seconds at most and normally a few seconds. After ultraviolet irradiation, optionally, the curing can be completely attained by heating. In the case of electron beam irradiation, an electron beam having energy in the range of 50 to 1,000 KeV is used and 2 to 5 Mrad dose of irradiation is preferable. Typically, an irradiation source having a lamp output on the order of 80 to 300 W/cm is utilized.

Since the alicyclic diepoxy compound represented by the general formula (I) that is an essential resin ingredient in the curable epoxy resin composition of the present invention (2) has low viscosity, the cured product thereof also has low viscosity and has excellent characteristics for processability. In addition, it dose not volatilize in the temperature region less than 100° C. and thus does not affect working surroundings.

It is to be noted that the alicyclic diepoxy compound represented by the general formula (I) that is an essential resin ingredient in the curable epoxy resin composition of the present invention (2) can produce various coatings, ink, adhesives, sealants, moldings or molded products, or an intermediate for other applications using such an alicyclic diepoxy compound, through homopolymerization or copolymerization, or by further reacting with other compounds. In addition, examples of an end use capable of employing the alicyclic diepoxy compound represented by the general formula (I) that is an essential resin ingredient in the curable epoxy resin composition of the present invention (2) include: agents for removing oxygen; coatings for furnitures; decorative coatings; undercoatings for automobiles; sealers; finishings; coatings for beverage cans and the other cans; inks for textual information or image information; sealants for electronic parts; photoresists suitable for developing printing boards or printed circuit boards; casting rolls for printing; glass composed mainly of unsaturated polyester and styrene; molded products of molding blends or sheet-forming blends reinforced with carbon, graphite, or other fibers; solvents; and flame retardants.

Hereinafter, the present invention (3) will be described in detail.

An alicyclic diepoxy compound (a) represented by the general formula (I) that is an essential resin ingredient in the epoxy resin composition for the encapsulation of electronic parts of the present invention (3) is the same as the alicyclic diepoxy compound (A) represented by the general formula (I) according to the present invention (2).

Another epoxy resin (e) added optionally to the alicyclic diepoxy compound (a) used in the present invention (3) is not specifically limited with respect to its molecular structure, molecular weight, and so on unless it has at least two epoxy groups in the molecule. Typically, an epoxy resin used for the encapsulation of semiconductors can be employed without being processed. In particular, examples of the other epoxy resins are the same as examples of another epoxy resin added optionally in the present invention (2) described above. One of or two or more of other epoxy resins may be mixed.

The content of another epoxy resin (e) added optionally is 10 to 90 parts by weight, preferably 15 to 35 parts by weight, more preferably 20 to 80 parts by weight based on 100 parts by weight of the total amount of the alicyclic diepoxy compound (a) represented by the general formula (I) and the epoxy resin (e).

If the content of another epoxy resin (e) added optionally is less than 10 parts by weight, there is a disadvantage in cost. In the case of the content beyond 90 parts by weight, the effect by the alicyclic diepoxy compound (a) is lower.

The curing agent (b) that is another essential ingredient in the present invention (3) is not particularly limited as long as it is an amine-based curing agent, an acid anhydride-based curing agent, phenol-based resin, or the like which reacts with an epoxy resin to cure the resin. Specific examples of the amine-based curing agent include aromatic diamines such as methaphenylene diamine, diaminodiphenylmethane, and diaminodiphenylsulfone. Specific examples of the acid anhydride-based curing agent include maleic anhydride, phthalic anhydride, and pyromellitic anhydride. Specific examples of the phenol-based resin curing agent include: aralkyl resins such as novolak phenol resins, cresol novolak resins, paraxylylene modified phenol resins, and paraxylylene/methaxylylene modified phenol resins; terpene modified phenol resins; dicyclopentadiene-modified phenol resins; and triphenol propane. However the curing agent is not limited to the above. The phenol-based resin curing agents are preferable in view of physical properties such as a coefficient of water absorption. Of those, a phenol aralkyl resin is particularly preferable.

The blending ratio of the alicyclic diepoxy compound (a) represented by the above formula (I), another epoxy resin (e) added optionally, and the curing agent (b) corresponds to the equivalent ratio of an epoxy group and a functional group in the curing agent (epoxy group/functional group) in the range of 0.5 to 2, preferably 0.6 to 1.2. The cured product, which is hardened under such a condition that the blending ratio has the equivalent ratio of less than 0.5 or above 2, has deteriorated moisture resistance, molding properties, and electrical characteristics, which is not preferable.

In addition, a curing accelerator (c) is not specifically limitated as long as it is a compound capable of accelerating the curing reaction of the epoxy resin and the curing agent. Examples of such the curing accelerator include, but not limited to: an amidine compound such as 1,8-diazabicyclo(5,4,0)undecene-7 (also referred to as DBU); an organic phosphorous compound such as triphenylphosphine (also refereed to as TPP) or tetraphenylphosphonium-tetraphenylborate; and an imidazole compound such as 2-methylimidazole. Such the curing accelerator can be used alone or mixed with another one. It is preferred that the blending quantity be in the range of 0.4 to 20 parts by weight based on 100 parts by weight of the total amount of the alicyclic diepoxy resin (a) represented by the general formula (I), another epoxy resin (e) added optionally, and the curing agent (b). If the blending quantity is less than 0.4 part by weight, sufficient curing properties may not be obtained in heat molding. On the other hand, if the blending quantity is beyond 20 parts by weight, it is anxious that the curing is so fast that undesirable failure in loading may occur owing to lower fluidity in molding.

Moreover, an inorganic filler (d) typically used for encapsulating materials can be used as an ingredient other than the curing accelerator (c). Specific examples thereof include fine fused silica powder, spherical fused silica powder, crystalline silica powder, secondarily-aggregated silica powder, alumina, aluminum hydroxide, and glass fiber and the like. Specifically, the spherical fused silica is preferable. Spherical silica preferably has as perfectly spherical shape as possible for improving fluidity and preferably has an extensive particle size distribution.

It is preferred that the blending quantity of the inorganic filler (d) be in the range of 200 to 2,400 parts by weight based on 100 parts by weight of the total amount of the alicyclic diepoxy compound (a) represented by the general formula (I), another epoxy resin (e) added optionally, and the curing agent (b). If the blending quantity is less than 200 parts by weight, it is anxious that the reinforcing effect by the inorganic filler may not be expressed sufficiently. A blending quantity beyond 2,400 parts by weight is not preferred because the fluidity of the resin composition may reduce to cause defective loading during molding or the deformation or disconnection of lead wires.

The epoxy resin composition for the encapsulation of electronic parts of the present invention, if necessary, may be appropriately blended with: a flame retardant such as a brominated epoxy resin, antimony oxide, or a phosphorus compound; an inorganic ion exchanger such as bismuth oxide hydrate; a coupling agent such as γ-glycidoxypropyl trimethoxysilane; a coloring agent such as carbon black oriron oxide; a stress-reducible agent such as silicone oil or silicone rubber; a mold release agent such as natural waxes, synthetic waxes, a higher fatty acid, or a metal salt thereof, or paraffin; an antioxidant; or any one of various additives such as a sodium salt or calcium salt of phosphoric acid or polyphosphoric acid; as well as the ingredients (a) to (e).

In order to prepare the epoxy resin composition for the encapsulation of electronic components of the present invention (3), after sufficient mixing of the alicyclic diepoxy compound (a) represented by the general formula (I), another epoxy resin (e) added optionally, the curing agent, the curing accelerator, a layered compound, an additional inorganic filler, and an additional additive using a mixer and so on, and further melt-kneading with a heat roll, a kneader, and so on, followed by cooling, the resultant mixture is pulverized. Additionally, for encapsulating electronic parts such as a semiconductor element to produce a semiconductor device, the encapsulation is performed by a molding method such as transfer molding, compression molding, or injection molding.

The epoxy resin composition for the encapsulation of electronic parts of the present invention (3) can be cured at temperatures of 65 to 200° C., preferably 75 to 190° C., more preferably 80 to 180° C. and for a curing time of 30 to 600 minutes, preferably 45 to 540 minutes, more preferably 60 to 480 minutes.

If the curing temperature and curing time are under the lower limits of the above-mentioned ranges, the curing is insufficient. In contrast, when they are above the upper limits of the above-mentioned ranges, the decomposition of the resin ingredients may occur. Thus, each of the cases is undesirable. The curing condition, which depends on various conditions, can be adjusted appropriately so that the curing time is shorter in the case of higher curing temperatures, and the curing time is longer in the case of lower curing temperatures.

Hereinafter, the present invention (4) will be described in detail.

An epoxy compound used in the present invention (4) is the alicyclic diepoxy compound represented by the general formula (I) which is the same as the alicyclic diepoxy compound represented by the general formula (I) used in the present inventions (2) and (3).

Of those, the alicyclic diepoxy compound where $R^1$ to $R^{18}$ are hydrogen atoms in the general formula (I) is preferable since it is industrially produced.

<Blending Ratio>

The addition amount of the alicyclic diepoxy compound represented by the general formula (I) which is used in the present invention (4) may be in the range of 0.05 to 15 parts by weight, preferably 0.5 to 10 parts by weight, more preferably 0.5 to 5 parts by weight based on 100 parts by weight of the components of the insulating oil. In the case of an addition amount of less than 0.05 part by weight, an effect for entrapping impurities in the component of the insulating oil and an effect for dispersing discharge energy are lacked so that there is no point of adding the compound. In contrast, an addition amount above 10 parts by weight is not preferred because the electrical characteristics of the insulating oil are reduced. Specifically, in a capacitor or the like, dielectric loss occurs within the inner portion thereof to generate heat, which lowers a function of the capacitor or the like.

<Description of Components in the Insulating Oil Utilized>

For example, a polyoxyalkylene glycol and a modification thereof, a neopentyl polyol ester, a dibasic acid ester, a polyester, and a fluorinated oil and the like can be applied. One of them can be used or one or more of them can be used as a mixture.

Components in the insulating oil will be specifically described. Examples of the polyoxyalkylene glycol include a polyoxypropylene glycol, a polyoxyethylene glycol, and a polyoxyethylene polyoxypropylene glycol, each of which preferably has a molecular weight of 200 to 3,000. Further, oxyethylene groups and oxypropylene groups in the polyoxyethylene polyoxypropylene glycol may be random and block.

Examples of available modifications of the polyoxyalkylene glycol include a polyoxyalkylene glycol monoalkylether, a polyoxyalkylene glycol dialkylether, a polyoxyalkylene glycol monoester, a polyoxyalkylene glycol diester, and alkylene oxide adducts of an alkylenediamine and the like. Specific examples of the modifications of the polyoxyaklylene glycol include: an ether of the polyoxyaklylene glycol and a linear or branched alkyl group having 1 to 18 carbon atoms; an ester of the polyoxyaklylene glycol and an aliphatic carboxylic acid having 2 to 18 carbon atoms; and propylene oxide adducts, ethylene oxide adducts, ethylene oxide propylene oxide random adducts, and ethylene oxide propylene oxide block adducts of ethylenediamine, diethylenetriamine, and triethylenetetramine. Further, examples of the modifications of the polyoxyalkylene glycol include polyoxyalkylene glycol glycerol triether and polyoxyalkylene glycol halides (particularly, chlorides are preferred).

Preferable examples of the neopentylpolyol ester include: esters of an aliphatic carboxylic acid having 2 to 18 carbon atoms, preferably 2 to 9 carbon atoms with neopentylpolyol; and esters of the aliphatic carboxylic acid with trimethylolpropane, pentaerythritol, dipentaerythritol, and tripentaerythritol.

Preferable examples of the dibasic acid ester include esters of a dicarboxylic acid having 4 to 12 carbon atoms with a primary or secondary alcohol having 4 to 18 carbon atoms. Specific examples thereof include butylphthalate and dihexylphthalate and the like.

Polyester can include compounds described in JP 3-128991 A, JP 3-128992 A, and so on, for example, polyester constituted of a divalent alcohol having 5 to 12 carbon atoms and/or a polyvalent alcohol which is trivalent or more having 15 or less carbon atoms and a mono-fatty acid having 2 to 18 carbon atoms and/or a polybasic acid having 4 to 14 carbon atoms.

Fluoridated oil can include perfluoroether and so on described in JP 3-7798 A.

In a stabilizer for an electrical insulating oil of the present invention (4), in addition to the above alicyclic diepoxy compound represented by the general formula (I), an extreme-pressure agent such as tricresyl phosphate, or an antioxidant such as α-naphthylbenzylamine, phenothiazine, or BHT can be used in the range of an addition amount, if desired within the scope of the present invention (4).

Hereinafter, the present invention (5) will be described in detail.

A casting epoxy resin composition for electrical insulation (hereinafter, referred to as "a casting epoxy resin composition") of the present invention (5) can be obtained using a thermosetting resin constituted of an epoxy resin composition containing a particular epoxy compound (ingredient A), an acid anhydride (ingredient B), and a curing accelerator (ingredient C), and an inorganic filler (ingredient D).

The above epoxy resin composition containing a particular epoxy compound (ingredient A) is composed of an alicyclic diepoxy compound (a-1) represented by the general formula (I) and the other epoxy compound (a-2).

The above alicyclic diepoxy compound (a-1) is the same as one represented by the general formula (1) used in the present inventions (2) to (4). Of those, the alicyclic diepoxy compound in which $R^1$ to $R^{18}$ are hydrogen atoms, that is, bicyclohexyl-3,3'-diepoxide is preferably used.

For the blending ratio of the alicyclic diepoxy compound (a-1) represented by the general formula (I) and the other epoxy compound (a-2), (a-1) must account for 5 to 80% by weight (hereinafter, abbreviated to "%"), preferably 8 to 75% by weight, and (a-2) must account for 95 to 20%, preferably 92 to 25% by weight, respectively of the total epoxy resin composition (ingredient A).

A specific example of (a-2) includes the same one as another epoxy resin added optionally of the present inventions (2)-(3) described above.

In the present invention (5), the epoxy resin composition (ingredient A) is constructed using two epoxy compounds as described above. In addition, by using an acid anhydride, a curing accelerator, and an inorganic filler, the casting epoxy resin composition for electrical insulation can be obtained, which provides a cured product having excellent electrical characteristics and mechanical properties without loss of desired workability for casting.

The acid anhydride (ingredient B) used along with the above epoxy resin composition (ingredient A) acts as a curing agent for the above epoxy resin composition (ingredient A), and is not particularly limited. Conventionally known one, that is, an acid anhydride as illustrated in the present invention (2) can be used as such an acid anhydride.

Each of such acid anhydrides can be used alone or two or more of them can be used in combination. Of those, methylhexahydrophthalic anhydride, tetrahydrophthalic anhydride, methylnorbornenedicarboxylic anhydride, and the like are preferably used because they have excellent heat resistance, and further improved electrical characteristics and mechanical strength.

The blending ratio of the above acid anhydride (ingredient B) must be defined in the range of 0.6 to 1.0 equivalent based on 1 equivalent of the epoxy resin composition (A) containing the alicyclic diepoxy compound (a-1) represented by the above general formula (I) and the epoxy compound (a-2) except (a-1). 0.7 to 0.9 equivalent is particularly preferable. That is, when the blending ratio of the acid anhydride is beyond 1.0 equivalent weight, electrical characteristics are deteriorated. In contrast, in the case of a blending ratio of less than 0.6 equivalent, heat resistance is lowered. The equivalent of the above acid anhydride (ingredient B) (acid anhydride equivalent) is defined as follows: the case where an acid anhydride group in the acid anhydride is one for one epoxy group in ingredient A is referred to as 1 equivalent; 0.6 to 1.0 equivalent of the above blending ratio refers to the case where the number of acid anhydride groups in the acid anhydride is 0.6 to 1.0 based on one epoxy group in the epoxy resin composition (ingredient A) containing two epoxy compounds (a-1) and (a-2).

Examples of the curing accelerator (ingredient C) used along with the above ingredient A and ingredient B include: tertiary amines such as benzyldimethylamine, trisdimethylaminomethylphenol, and triethylenediamine; bromine salts of quaternary amines such as tetrabutylammonium bromide; diazabicycloundecene (DBU) and an organic acid salt of DBU; triphenylphosphine; phosphoric ester; borate ester; Lewis acid; alkoxide and acetylacetone of titanium and aluminum; an organometallic compound such as an acetoacetic ester; and imidazoles. Each of such curing accelerators can be used alone or two or more of them can be used in combination. Tertiary amines and bromine salts of quaternary amines described above are preferably used since the resultant cured product has excellent heat resistance.

Their commercially available products include SA-102 (a diazabicycloundecene-based curing accelerator), SA-506 (a diazabicycloundecene-based curing accelerator), and U-CAT5003 (a phosphonium salt-based curing accelerator) (all from SAN-APRO Ltd).

The blending quantity of the above curing accelerator (ingredient C) is preferably defined in the range of 0.5 to 10 parts by weight based on 100 parts by weight in total of the epoxy resin composition (ingredient A) containing two epoxy compounds described above. That is, if the blending quantity of the ingredient C is less than 0.5% part by weight, the curing reaction is slow, which leads to a problem with workability. If the blending quantity is beyond 10 parts by weight, the reaction time is significantly short, which may cause reduction in fluidity and cause volume resistivity electrically.

Examples of the inorganic filler, which is the ingredient (D), used as an essential ingredient along with the above ingredients A to C include silica, alumina, talc, silica sand, calcium carbonate, and barium sulfate. Each of such inorganic fillers can be used alone or two or more of them can be used in combination. Of those, spherical fused silica powder of silica and fused alumina of alumina are preferably used in view of excellent tan δ and withstand voltage characteristics. That is, out of silica, the use of spherical fused silica powder results in further improvement in a dielectric dissipation factor (tan δ) and withstand voltage characteristics through the action of restraining interfacial polarization and avoiding the concentration of electric stress. Especially, in the case of using above spherical fused silica, one in which particles each having a particle size of 50 µm or less makes up 99% by weight or more of the total [a requirement (X)], and has an average particle size of 35 µm or less [a requirement (Y)] is preferably used, since reduction in workability for casting by increased viscosity can be effectively prevented and thus the casting epoxy resin composition having excellent electrical characteristics and mechanical strength can be obtained. Alternatively, fused alumina can be generally obtained by dissolving Bayer-process alumina or bauxite as a main raw material in an electric furnace and performing a series of process (precipitation, burning, pulverization, deferrization, rinsing, and drying). By using such fused alumina, both electrical characteristics and mechanical properties can be enhanced as in the use of the above fused silica. Specifically, withstand voltage characteristics are significantly improved as compared to the use of electrically fused alumina.

It is essential to define the blending quantity of the above inorganic filler (D) in the range of 30 to 80% by weight of the total of ingredients (A) to (D) of the casting epoxy resin composition for electrical insulation of the present invention (5). That is, if the blending quantity of the inorganic filler (D) is less than 30% of the entire composition, the casting epoxy resin composition for electrical insulation of the present invention is significantly reduced in melt viscosity, which causes the precipitation of the inorganic filler (D). In addition, the mechanical strength is lowered. In contrast, a blending quantity beyond 80% may lead to too high viscosity, which reduces mixing properties and fluidity, and it is anxious that this causes reduction in workability.

In addition to the above ingredients A to C and the inorganic filler that is ingredient (D), optionally, other additives such as a diluent, a plasticizer, a pigment, a mold release agent, and a flame retardant can be appropriately blended into the casting epoxy resin composition for electrical insulation of the present invention (5).

Thus, in order to prepare the casting epoxy resin composition for electrical insulation of the present invention (5), each of the above raw materials is blended in the predetermined rate. For blending, a conventionally known mixing machine such as a dry blender, a ribbon blender, or a Henschel mixer can be used. Typically, blending is performed at normal temperature.

The formulation of each of the above components is prepared as the casting resin composition for electrical insulation by agitating and mixing under vacuum heating while removing air bubbles. The temperature for agitating and mixing is generally set at 40 to 100° C.

If the setting temperature during preparation is less than 40° C., agitating and mixing operations find difficulty in obtaining uniformity, because of too high viscosity. In contrast, if the temperature during preparation is beyond 100° C., a curing reaction unwillingly occurs so that a normal casting resin composition for electrical insulation cannot be obtained. For agitating and mixing, an ordinary machine such as a single-screw or multiscrew extruder or a kneader which is provided with a pressure reducing device can be used.

Then, the casting epoxy resin composition for electrical insulation which has been prepared is injected into a defined molding die and cured by heating under a predetermined condition to form a cured product of the present invention (5) having a desired shape.

The casting epoxy resin composition for electrical insulation of the present invention (5) can be cured at temperatures of 100 to 200° C., preferably 100 to 190° C., more preferably 100 to 180° C., and for a curing time of 30 to 600 minutes, preferably 45 to 540 minutes, more preferably 60 to 480 minutes.

If the curing temperature and curing time are under the lower limits of the above-mentioned ranges, the curing is insufficient. In contrast, when they are above the upper limits of the above-mentioned ranges, the decomposition of the resin ingredient may occur. Thus, each of the cases is undesirable. The curing condition, which depends on various conditions, can be adjusted appropriately so that the curing time is shorter in the case of higher curing temperatures, and the curing time is longer in the case of lower curing temperatures.

EXAMPLES

Examples and Comparative Examples for Invention (1)

The following examples are used for illustrations of the present invention, and they do not restrict the scope at all.

Example 1

In a reactor, 406 g of bicyclohexyl-3,3'-diene, which is an alicyclic olefin compound represented by the above general formula (II), and 1,217 g of ethyl acetate were placed. While nitrogen was flown into a gas phase part and the temperature in the reaction system was controlled at 37.5° C., 457 g of an ethyl acetate solution (water content: 0.41% by weight) containing peracetic acid at 30% by weight was added dropwise for about 3 hours. After the completion of dropwise addition of the peracetic acid solution, the resulting mixture was aged at 40° C. for 1 hour to complete the reaction. The crude liquid at the completion of the reaction was then washed with water at 30° C., and treated at 70° C./20 mmHg to remove low-boiling-point compounds. Consequently, 415 g of an epoxy compound was obtained with an yield of 85%.

The oxirane oxygen content of the epoxy compound obtained was 14.7% by weight (theoretical value: 16.5% by weight).

In $^1$HNMR analysis, a peak at about δ4.5 to 5 ppm originating from the inner double bond disappeared, and the formation of a proton peak at about δ3.1 ppm originating from the epoxy group was observed. It was confirmed that the epoxy compound was an alicyclic diepoxy compound represented by the above general formula (I). FIG. 1 shows the NMR chart of the obtained alicyclic epoxy compound.

Example 2

243 g of bicyclohexyl-3,3'-diene, which is an alicyclic olefin compound represented by the above general formula (II), and 730 g of ethyl acetate were placed. While nitrogen was flown into a gas phase part and the temperature in the reaction system was controlled at 37.5° C., 274 g of an ethyl acetate solution (water content: 0.41% by weight) containing peracetic acid at 30% by weight was added dropwise for about 3 hours. After the completion of dropwise addition of peracetic acid solution, the resulting mixture was aged at 40° C. for 1 hour to complete the reaction. The crude liquid at the completion of the reaction was then washed with water at 30° C., and treated at 70° C./20 mmHg to remove low-boiling-point compounds. Consequently, 270 g of an epoxy compound was obtained with an yield of 93%.

The oxirane oxygen content of the epoxy compound obtained was 15.3% by weight.

In $^1$HNMR analysis, a peak at about δ4.5 to 5 ppm originating from the inner double bond disappeared, and the formation of a proton peak at about δ3.1 ppm originating from the epoxy group was observed. It was confirmed that the epoxy compound was an alicyclic diepoxy compound represented by the above general formula (I).

Comparative Example 1

25 g of bicyclohexyl-3,3'-diene, which is an alicyclic olefin compound represented by the above general formula (II), and 20 g of ethyl acetate were placed. While nitrogen was flown into the gas phase part and the temperature in the reaction system was controlled at 60° C., 36 g of hydrogen peroxide solution at 30% by weight was added dropwise for about 1 hour. After the completion of dropwise addition of hydrogen peroxide solution, the resulting mixture was aged at 60° C. for 12 hours to complete the reaction.

In $^1$HNMR analysis of the reaction crude liquid, the peak at about δ4.5 to 5 ppm originating from the inner double bond did not disappear, and the formation of a proton peak at about δ3.1 ppm originating from the epoxy group was not observed. No alicyclic diepoxy compound represented by the above general formula (I) was formed.

Comparative Example 2

25 g of bicyclohexyl-3,3'-diene, which is an alicyclic olefin compound represented by the above general formula (II), 135 g of benzene, and 0.07 g of molybdenum pentachloride as a catalyst were placed. While nitrogen was flown into the gas phase part and the temperature in the reaction system was controlled at 80° C., 120 g of benzene solution containing t-butyl hydroperoxide at 30% by weight was added dropwise for about one hour. After the completion of dropwise addition of benzene solution containing t-butyl hydroperoxide, the resulting mixture was aged at 80° C. for 3 hours to complete the reaction. The crude liquid at the completion of the reaction was then washed with water at 30° C., and treated at 70° C./20 mmHg to remove low-boiling-point compounds. 25.3 g of an epoxy compound was obtained with an yield of 84.6%.

The oxirane oxygen content of the epoxy compound obtained was 12.6% by weight.

In $^1$HNMR analysis, the peak at about δ4.5 to 5 ppm originating from the inner double bond disappeared, and the formation of a proton peak at about δ3.1 ppm originating from the epoxy group was observed. Though it was confirmed that the epoxy compound was an alicyclic diepoxy compound represented by the above general formula (I), it was also confirmed that the yield of the alicyclic diepoxy compound obtained was low compared with Examples 1 and 2, and the oxirane oxygen content was also low.

According to the present invention (1), the alicyclic diepoxy compound represented by the general formula (I) can be produced from the alicyclic olefin compound represented by the above general formula (II) at low cost, in high yield, and in high purity.

Examples and Comparative Examples for Invention (2)

Example 3

100 parts by weight of the alicyclic diepoxy compound obtained by Example 1 as the ingredient (A) was mixed with 0.6 part by weight of "San-Aid SI-60L" (a sulfonium salt-based photocationic polymerization initiator manufactured by Sanshin Chemical Industry CO., Ltd.) as the ingredient (B) to form a composition. The viscosity of the composition was measured at 25° C. using a type E rotational viscometer (manufactured by Tokyo Precision Instrument Co., Ltd.), and it was 50 mPa·s.

The above resin composition was placed for the measurement under an air atmosphere at 200 ml/minute and at an increasing temperature of 10° C./minute from 40 to 200° C. using a TG/DTA device (EXSTAR6000TG/DTA6200, manufactured by Seiko Instruments Inc.; same in the following) to measure the temperature at which the resin composition showed weight reduction either due to volatilization of the resin composition by heating or due to degradation of the cured resin. The weight reduction at 100° C. was less than 0.5%, and a weight reduction of 5% as compared to the original weight was observed at 150.0° C.

Comparative Example 3

100 parts by weight of 3,4-epoxycyclohexenylmethyl-3', 4'-epoxycyclohexenyl carboxylate (Celloxide 2021P, manufactured by Daicel Chemical Industries, Co., Ltd; depicted as CEL 2021P in the tables) was mixed with 0.6 part by weight of "San-Aid SI-60L" to form a composition. The viscosity of the composition was measured at 25° C. using the type E rotational viscometer (manufactured by Tokyo Precision Instrument Co., Ltd.), and it was 240 mPa·s.

The above resin composition was placed for the measurement under an air atmosphere at 200 ml/minute and at an increasing temperature of 10° C./minute from 40 to 250° C. using a TG/DTA device to measure the temperature at which the resin composition showed weight reduction either due to volatilization of the resin composition by heating or due to degradation of the cured resin. The weight reduction at 100° C. was less than 0.5%, and a weight reduction of 5% as compared to the original weight was observed at 210.8° C.

Comparative Example 4

100 parts by weight of ε-caprolactone-modified 3,4-epoxycyclohexenylmethyl-3',4'-epoxycyclohexenyl carboxylate (Celloxide 2081, manufactured by Daicel Chemical Industries, Co., Ltd; depicted as CEL 2081 in the tables) was mixed with 0.6 part by weight of "San-Aid SI-60L" to form a composition. The viscosity of the composition was measured at 45° C. using the type E rotational viscometer (manufactured by Tokyo Precision Instrument Co., Ltd.), and it was 90 mPa·s.

The above resin composition was placed for the measurement under an air atmosphere at 200 ml/minute and at an increasing temperature of 10° C./minute from 40 to 250° C. using a TG/DTA device to measure the temperature at which the resin composition showed weight reduction either due to volatilization of the resin composition by heating or due to degradation of the cured resin. The weight reduction at 100° C. was less than 0.5%, and a weight reduction of 5% as compared to the original weight was observed at 233.4° C.

Comparative Example 5

100 parts by weight of limonene diepoxide (Celloxide 3000, manufactured by Daicel Chemical Industries, Co., Ltd; depicted as CEL 3000 in the tables) was mixed with 0.6 part by weight of San-Aid SI-60L to form a composition. The viscosity of the composition was measured at 25° C. using the type E rotational viscometer (manufactured by Tokyo Precision Instrument Co., Ltd.), and it was 20 mPa·s.

The above resin composition was placed for the measurement under an air atmosphere at 200 ml/minute and at an increasing temperature of 10° C./minute from 40 to 120° C. using a TG/DTA device to measure the temperature at which the resin composition showed weight reduction either due to evaporation of the resin composition by heat or due to degradation of the cured resin. The weight reduction at 100° C. was 8.3%, and a weight reduction of 5% as compared to the original weight was observed at 96.2° C.

Comparative Example 6

100 parts by weight of ε-caprolactone-modified 3-cyclohexene-1,2-dicarboxylic acid bis3-cyclohexenyl methylester (Epolead GT301, manufactured by Daicel Chemical Industries, Co., Ltd) was mixed with 0.6 part by weight of San-Aid SI-60L to form a composition. The viscosity of the composition was measured at 75° C. using the type E rotational viscometer (manufactured by Tokyo Precision Instrument Co., Ltd.), and it was 300 mPa·s.

The above resin composition was placed for the measurement under an air atmosphere at 200 ml/minute and at an increasing temperature of 10° C./minute from 40 to 280° C. using a TG/DTA device to measure the temperature at which the resin composition showed weight reduction either due to volatilization of the resin composition by heating or due to degradation of the cured resin. The weight reduction at 100° C. was less than 0.5%, and a weight reduction of 5% as compared to the original weight was observed at 247.9° C.

Comparative Example 7

100 parts by weight of c-caprolactone-modified epoxidized butanetetracarboxylic acid tetrakis-3-cyclohexenylmethylester (Epolead GT403, manufactured by Daicel Chemical Industries, Co., Ltd) was mixed with 0.6 part by weight of San-Aid SI-60L to form a composition. The viscosity of the composition was measured at 75° C. using the type E rotational viscometer (manufactured by Tokyo Precision Instrument Co., Ltd.), and it was 800 mPa·s.

The above resin composition was placed for the measurement under an air atmosphere at 200 ml/minute and at an increasing temperature of 10° C./minute from 40 to 280° C. using a TG/DTA device to measure the temperature at which the resin composition showed weight reduction either due to volatilization of the resin composition by heating or due to degradation of the cured resin. The weight reduction at 100° C. was less than 0.5%, and a weight reduction of 5% as compared to the original weight was observed at 253.7° C.

TABLE 1

| | Example 3 | Comparative Example 3 | Comparative Example 4 | Comparative Example 5 | Comparative Example 6 | Comparative Example 7 |
|---|---|---|---|---|---|---|
| Bicyclohexyl-3,3'-epoxide | 100 parts | | | | | |
| CEL2021P | | 100 parts | | | | |
| CEL2081 | | | 100 parts | | | |
| CEL3000 | | | | 100 parts | | |
| Epolead GT301 | | | | | 100 parts | |
| Epolead GT403 | | | | | | 100 parts |
| San-Aid SI60L | 0.6 part | 0.6 part | 0.6 part | 0.6 part | 0.6 part | 0.6 part |
| Viscosity (mPa · s, 25° C.) | 50 | 240 | | 20 | | |
| Viscosity (mPa · s, 45° C.) | | | 90 | | | |
| Viscosity (mPa · s, 75° C.) | | | | | 300 | 800 |
| Percentage of weight reduction at 100° C. | Less than 0.5% | Less than 0.5% | Less than 0.5% | 8.30% | Less than 0.5% | Less than 0.5% |
| 5% thermal degradation temperature(° C.) | 150.0 | 210.8 | 233.4 | 96.2 | 247.9 | 253.7 |
| Workability at room temperature | ⊚ | ○ | Δ | ⊚ | X | X |
| Safeness in working and moldability | ○ | ○ | ○ | X | ○ | ○ |

Table 1 shows the mixing ratios of the respective ingredients in Example 3 and Comparative Examples 3 to 7, and the obtained results.

As is evident from Table 1, the resin composition in the Example 3 shows low viscosity and excellent workability. Although the resin composition in Comparative Example 5 shows low viscosity, it shows a large weight reduction by heating and a low thermal decomposition temperature of 96.2° C., indicating insufficient heat tolerance. In addition, while the resin compositions of Comparative Examples 6 and 7 appears to have high thermal decomposition temperatures and to be excellent in heat resistance, they have too high viscosity even when heated at 75° C., indicating insufficient moldability.

Example 4

100 parts by weight of the alicyclic diepoxy compound obtained by Example 1 as the ingredient (A) was mixed with 0.3 part by weight of San-Aid SI-60L (manufactured by Sanshin Chemical Industry Co., Ltd.) as the ingredient (B) to form a resin composition. The reactivity of the resin composition was measured by using the Rapra Scanning Vibrating Needle Curemeter SVNC (Scanning VNC) at 80° C. with the default settings of the device (Dwell=250 ms, Frequency Filter=50 Hz, Amplitude Filter=250, Stop Time=1:0 hr:min.) as main measurement conditions. Temperature was raised for about 3 minutes to the measurement temperature and the measurement was started when it reached 80° C. A resonance frequency was about 66 Hz at the onset of the measurement. Then, as the resin composition cured, the resonance frequency changed. The time point when the resonance frequency reached 100 Hz was recorded. It was 22 minutes and 51 seconds.

Comparative Example 8

100 parts by weight of Celloxide 2021P (manufactured by Daicel Chemical Industries Co., Ltd; depicted as CEL 2021P in the tables) was mixed with 0.3 part by weight of SI-100L (a sulfonium salt-based cationic polymerization initiator, manufactured by Sanshin Chemical Industry Co., Ltd.) to form a resin composition. The reactivity of the resin composition was measured by using the Rapra Scanning Vibrating Needle Curemeter SVNC (Scanning VNC) at 80° C. with the default settings of the device (Dwell=250 ms, Frequency Filter=50 Hz, Amplitude Filter=250, Stop Time=1:0 hr:min.) as main measurement conditions. Temperature was raised for about 3 minutes to the measurement temperature of 80° C. and the measurement was started when it reached 80° C. The resonance frequency was about 66 Hz at the onset of the measurement. Then, as the resin composition cured, the resonance frequency changed. The time point when the resonance frequency reached about 100 Hz was recorded. It was 50 minutes and 49 seconds.

Table 2 shows the mixing ratios for the respective ingredients in Example 4 and Comparative Example 8, and the obtained results.

TABLE 2

|  | Example 4 | Comparative Example 8 |
| --- | --- | --- |
| Bicyclohexyl-3,3'-epoxide | 100 parts |  |
| CEL2021P |  | 100 parts |
| San-Aid 60L | 0.3 part | 0.3 part |
| Time to SVNC 100 Hz | 22 minutes 51 seconds | 50 minutes 49 seconds |
| Reactivity with cationic catalyst | ◉ | ○ |

As is evident from Table 2, the reactivity of the resin composition in Example 4 is twice or more as good as that in Comparative Example 8.

Example 5

100 parts by weight of the alicyclic diepoxy compound obtained in the Example 1 as the ingredient (A) was mixed with 0.6 part by weight of San-Aid SI-60L (manufactured by Sanshin Chemical Industry Co., Ltd.) as the ingredient (B) to form a resin composition. The viscosity of the composition was measured at 25° C. using the type E rotational viscometer (manufactured by Tokyo Precision Instrument Co., Ltd.), and it was 50 mPa·s. About 10 g of the resin composition was poured into an aluminum cup of 54 mm in diameter and 15 mm in depth, and subjected to first curing (curing temperature: 35° C.; curing time: 5 hours), followed by second curing (curing temperature: 150° C.; curing time: 1 hour) to produce a transparent colorless cured resin.

The coefficient of linear expansion of the cured resin was measured according to JIS K 7197. The glass transition temperature was obtained as the point where a change in the coefficient of linear expansion was observed by extrapolation. The measurement of the glass transition point was done in the range of 40 to 400° C. in two samples cut out from the same casted product. No change in the coefficient of linear expansion was detected, and the glass transition temperature was too high to be confirmed.

The cured resin was placed for the measurement under an air atmosphere at 200 ml/minute and at an increasing temperature of 10° C./minute from 40 to 400° C. using a TG/DTA device to measure the temperature at which the cured resin showed weight reduction due to the degradation by heating. A weight reduction of 3% in comparison with the original weight was observed at 272.6° C., and a weight reduction of 5% was observed at 288.1° C.

Example 6

100 parts by weight of the alicyclic diepoxy compound obtained in the Example 1 as the ingredient (A) was mixed with 139.1 parts by weight of methylhexahydrophthalic anhydride (RIKACID MH-700, manufactured by New Japan Chemical Co., Ltd.) as the ingredient (C), 1 part by weight of ethylene glycol as an initiator, and 0.5 part by weight of DBU [1,8-diazabicyclo(5,4,0)undecene] as a curing accelerator to form a resin composition. The viscosity of the composition was measured at 25° C. using the type E rotational viscometer (manufactured by Tokyo Precision Instrument Co., Ltd.), and it was 60 mPa·s. About 10 g of the resin composition was poured into an aluminum cup of 54 mm in diameter and 15 mm in depth, and subjected to first curing (curing temperature: 110° C.; curing time: 2 hours), followed by second curing (curing temperature: 150° C.; curing time: 1 hour) to produce a transparent colorless cured resin.

The coefficient of linear expansion of the cured resin was measured according to JIS K 7197. The glass transition temperature was obtained as the point where a change in the coefficient of linear expansion was observed by extrapolation. The measurement of the glass transition temperature was done in the range of 40 to 400° C. in two samples cut out from the same cast product. The glass transition temperature was 120.4° C.

The cured resin was placed for the measurement under an air atmosphere at 200 ml/minute and at an increasing temperature of 10° C./minute from 40 to 400° C. using a TG/DTA device to measure the temperature at which the cured resin showed weight reduction due to the degradation by heating.

A weight reduction of 3% in comparison with the original weight was observed at 197.9° C., and a weight reduction of 5% was observed at 231.7° C.

Example 7

100 parts by weight of the alicyclic diepoxy compound obtained in the Example 1 as the ingredient (A) was mixed with 139.1 parts by weight of RIKACID MH-700 manufactured by New Japan Chemical Co., Ltd. as the ingredient (C), 1 part by weight of ethylene glycol as an initiator, and 0.5 part by weight of DBU [1,8-diazabicyclo(5,4,0)undecene] as a curing accelerator to form a resin composition. The viscosity of the composition was measured at 25° C. using the type E rotational viscometer (manufactured by Tokyo Precision Instrument Co., Ltd.), and it was 60 mPa·s. About 10 g of the resin composition was poured into an aluminum cup of 54 mm in diameter and 15 mm in depth, and subjected to first curing (curing temperature: 110° C.; curing time: 2 hours), followed by second curing (curing temperature: 180° C.; curing time: 1 hour) to produce a transparent colorless cured resin.

The coefficient of linear expansion of the cured resin was measured according to JIS K 7197. The glass transition temperature was obtained as the point where a change in the coefficient of linear expansion was observed by extrapolation. The measurement of the glass transition temperature was done in the range of 40 to 400° C. in two samples cut out from the same casted product. The glass transition temperature was 121.0° C.

The cured resin was placed for the measurement under an air atmosphere at 200 ml/minute and at an increasing temperature of 10° C./minute from 40 to 400° C. using a TG/DTA device to measure the temperature at which the cured resin showed weight reduction due to the degradation by heating.

A weight reduction of 3% in comparison with the original weight was observed at 223.0° C., and a weight reduction of 5% was observed at 253.9° C.

Example 8

100 parts by weight of the alicyclic diepoxy compound obtained in the Example 1 as the ingredient (A) was mixed with 139.1 parts by weight of RIKACID MH-700 manufactured by New Japan Chemical Co., Ltd. as the ingredient (C), 1 part by weight of ethylene glycol as an initiator, and 0.5 part by weight of DBU [1,8-diazabicyclo(5,4,0)undecene] as a curing accelerator to form a resin composition. The viscosity of the composition was measured at 25° C. using the type E rotational viscometer (manufactured by Tokyo Precision Instrument Co., Ltd.), and it was 60 mPa·s. About 10 g of the resin composition was poured into an aluminum cup of 54 mm in diameter and 15 mm in depth, and subjected to first curing (curing temperature: 120° C.; curing time: 1 hour), followed by second curing (curing temperature: 180° C.; curing time: 2 hours) to produce a transparent colorless cured resin.

The coefficient of linear expansion of the cured resin was measured according to JIS K 7197. The glass transition temperature was obtained as the point where a change in the coefficient of linear expansion was observed by extrapolation. The measurement of the glass transition temperature was done in the range of 40 to 400° C. in two samples cut out from the same casted product. The glass transition temperature was 205.4° C.

The cured resin was placed for the measurement under an air atmosphere at 200 ml/minute and at an increasing temperature of 10° C./minute from 40 to 400° C. using a TG/DTA device to measure the temperature at which the cured resin showed weight reduction due to the degradation by heating.

A weight reduction of 3% in comparison with the original weight was observed at 233.6° C., and a weight reduction of 5% was observed at 270.8° C.

Comparative Example 9

100 parts by weight of Celloxide 2021P (manufactured by Daicel Chemical Industries, Ltd; depicted as CEL 2021P in the tables) was mixed with 0.6 part by weight of SI-100L (manufactured by Sanshin Chemical Industry Co., Ltd.) to form a resin composition. The viscosity of the composition was measured at 25° C. using the type E rotational viscometer (manufactured by Tokyo Precision Instrument Co., Ltd.), and it was 240 mPa·s. About 10 g of the resin composition was poured into an aluminum cup of 54 mm in diameter and 15 mm in depth, and subjected to first curing (curing temperature: 65° C. because the resin composition did not cure at a temperature of 60° C. or lower; curing time: 2 hours), followed by second curing (curing temperature: 150° C.; curing time: 1 hour) to produce a transparent colorless cured resin.

The coefficient of linear expansion of the cured resin was measured according to JIS K 7197. The glass transition temperature was obtained as the point where a change in the coefficient of linear expansion was observed by extrapolation. The measurement of the glass transition temperature was done in the range of 40 to 400° C. in two samples cut out from the same casted product. The glass transition temperature was 159.8° C.

The cured resin was placed for the measurement under an air atmosphere at 200 ml/minute and at an increasing temperature of 10° C./minute from 40 to 400° C. using a TG/DTA device to measure the temperature at which the cured resin showed weight reduction due to the degradation by heating.

A weight reduction of 3% in comparison with the original weight was observed at 217.5° C., and a weight reduction of 5% was observed at 257.5° C.

Comparative Example 10

100 parts by weight of Celloxide 2021P (manufactured by Daicel Chemical Industries Co., Ltd; depicted as CEL 2021P in the tables) was mixed with 139.1 parts by weight of RIKACID MH-700 (manufactured by New Japan Chemical Co., Ltd.), 1 part by weight of ethylene glycol, and 0.5 part by weight of DBU [1,8-diazabicyclo(5,4,0)undecene] to form a resin composition. The viscosity of the composition was measured at 25° C. using the type E rotational viscometer (manufactured by Tokyo Precision Instrument Co., Ltd.), and it was 110 mPa·s.

About 10 g of the resin composition was poured into an aluminum cup of 54 mm in diameter and 15 mm in depth, and subjected to first curing (curing temperature: 120° C.; curing time: 1 hour), followed by second curing (curing temperature: 180° C.; curing time: 2 hours) to produce a transparent colorless cured resin.

The coefficient of linear expansion of the cured resin was measured according to JIS K 7197. The glass transition temperature was obtained as the point where a change in the coefficient of linear expansion was recognized by extrapolation. The measurement of the glass transition temperature was done in the range of 40 to 400° C. in two samples cut out from the same casted product. The glass transition temperature was 221.5° C.

The cured resin was placed for the measurement under an air atmosphere at 200 ml/minute and at an increasing temperature of 10° C./minute from 40 to 400° C. using a TG/DTA device to measure the temperature at which the cured resin showed weight reduction due to the degradation by heating.

A weight reduction of 3% in comparison with the original weight was observed at 294.9° C., and a weight reduction of 5% was observed at 304.8° C.

Table 3 shows the mixing ratios of the respective ingredients in Examples 5 to 8 and Comparative Examples 9 and 10, and the obtained results.

TABLE 3

|  | Example 5 | Example 6 | Example 7 | Example 8 | Comparative Example 9 | Comparative Example 10 |
|---|---|---|---|---|---|---|
| Bicyclohexyl-3,3'-epoxide CEL2021P | 100 parts | 100 parts | 100 parts | 100 parts | | |
| San-Aid SI-60L | 0.6 part | | | | 100 parts | 100 parts |
| MH-700 | | 139.1 parts | 139.1 parts | 139.1 parts | 0.6 part | 139.1 parts |
| Ethylene glycol | | 1 part | 1 part | 1 part | | 1 part |
| DBU | | 0.5 part | 0.5 part | 0.5 part | | 0.5 part |
| Viscosity | 50 mPa·s | 60 mPa·s | 60 mPa·s | 60 mPa·s | 240 mPa·s | 110 mPa·s |
| First curing condition | 35° C., 5 hours | 110° C., 2 hours | 110° C., 2 hours | 120° C., 1 hour | 65° C., 2 hours | 120° C., 1 hour |
| Second curing condition | 150° C., 1 hour | 150° C., 1 hour | 150° C., 1 hour | 180° C., 2 hours | 150° C., 1 hour | 180° C., 2hours |
| Glass transition point (° C.) | Not observed in TMA, DSC | 120.4 | 121.0 | 205.4 | 159.8 | 221.5 |
| 3% thermal degradation temperature(° C.) | 272.6 | 197.9 | 223 | 233.6 | 217.5 | 294.9 |
| 5% thermal degradation temperature(° C.) | 288.1 | 231.7 | 263.9 | 270.8 | 257.5 | 304.8 |
| Heat resistance | ⊚ | X | X | ○ | Δ | ○ |

As is evident from Table 3, the glass transition point of the cured product in Example 5 is too high to measure, indicating superiority to that in Comparative Example 9 conducted under similar conditions. In addition, the viscosities of all the compositions in Examples 5 to 8 are lower than those in Comparative Examples 9 and 10, confirming the easiness in handling.

The alicyclic diepoxy compound represented by the formula (I), which is the essential resin ingredient (A) in the curable epoxy resin composition of the present invention (2) shows increased reactivity with cationic catalysts because it has no ester group in the molecule. Therefore, it has an effect of lowering the curing temperature or of reducing the curing time relative to those that were necessary for conventional compositions.

The curable epoxy resin composition that contains, as an essential ingredient, an alicyclic diepoxy compound of the present invention (2), which has low viscosity and easiness in handling, has high reactivity to various curing agents, low viscosity, and excellent workability. In addition, it is also superior in that it has less effect on the working surroundings.

Compared with cured products obtained by curing conventional epoxy resins, a cured product obtained by curing the curable epoxy resin composition shows very good performance in transparency, heat resistance, and the like. Moreover, the cured product shows useful physical properties in various fields including uses in coatings, ink, adhesives, sealants, and encapsulants and the like.

Examples and Comparative Examples for Invention (3)

Herein, the respective ingredients were mixed and mulled to prepare molding materials. The molding materials were characterized by measuring their spiral flow, cure torque, and coefficient of water absorption. The measuring method and conditions of each property were as follows.

1. Spiral Flow

The molding materials immediately after the preparation were used for the measurement with a metal mold for the spiral flow measurement according to EMMI-1-66, at metal-mold temperature of 175° C., injection pressure of 70 kgf/cm$^2$, and curing time of 2 minutes. Spiral flow (cm) is a parameter for fluidity, and the larger values indicate the better fluidity.

2. Torque Through Curing

The prepared molding materials were heated at 175° C. for 45 seconds and then used for the measurement of torque with a curastometer (JSR Curastometer PS type, manufactured by Orientech Co., Ltd.). The torque value (kgf·cm) by the curastometer is a parameter for hardness, and the larger values indicate the higher hardness.

3. Coefficient of Water Absorption

The molding materials were molded into discs having diameter of 50 mm and thickness of 3 mm using a transfer molding machine at metal-mold temperature of 175° C., injection pressure of 75 kg/cm$^2$, and curing time of 2 minutes. After post-curing at 175° C. for 8 hours, the disks were soaked in distilled water at 23° C. for 24 hours. The coefficient of water absorption (% by weight) was measured as the weight change.

Example 9

Respective ingredients were kneaded in the following mixing ratio, mulled using a heat roll at 95° C. for 8 minutes, cooled, and crushed to obtain a resin composition. The evaluation results are as shown in Table 4.

The mixing ratio was 5 parts by weight of the alicyclic diepoxy compound obtained in Example 1 as the ingredient (a), 95 parts by weight of resin which is mainly composed of a biphenyl-based epoxy resin (a cresol novolak-based epoxy resin EOCN-1020, manufactured by Nippon Kayaku Ltd.; epoxy equivalent: 185; melting point: 105° C.) as the ingredient (e) added optionally, 51.8 parts by weight of a phenol resin (Phenol Resin PR-53195, manufactured by Sumitomo Bakelite Ltd.; hydroxyl equivalent: 167; softening point: 73° C.) as the ingredient (b), 1.2 part by weight of 1,8-diazabicyclo(5,4,0)undecene-7(DBU) as the ingredient (c), 725 parts by weight of a fused silica sphere (an average particle size of 15 μm), 2 parts by weight of carbon black, and 2 parts by weight of carnauba wax.

Examples 10 to 13

The molding materials were prepared by a similar operation to Example 9 with respective ingredients in the mixing ratios shown in Table 4. The evaluation results are summarized in Table 4.

Comparative Examples 11 to 12

The molding materials were prepared by a similar operation to Example 9 with respective ingredients in the mixing ratios shown in Table 4 (continued), and they were individually evaluated. The evaluation results are summarized in Table 4 (continued).

TABLE 4

|  | Example 9 | Example 10 | Example 11 | Example 12 | Example 13 |
|---|---|---|---|---|---|
| Epoxy compound in Example 1 | 5 | 30 | 60 |  |  |
| Epoxy compound in Example 2 |  |  |  | 20 | 75 |
| EOCN-1020 | 95 | 70 | 40 | 80 | 25 |
| PR-53195 | 51.8 | 64.8 | 79.7 | 60.5 | 90.7 |
| DBU | 1.2 | 1.0 |  | 1.4 |  |
| TPP |  |  | 0.9 |  | 0.9 |
| Fused silica sphere | 725 | 787 | 880 |  |  |
| Crushed Silica |  |  |  | 802 | 950 |
| Carbon black | 2 | 2 | 2.5 | 2 | 2.5 |
| Carnauba wax | 2 | 2 | 2.5 | 2 | 2.5 |
| Spiral flow | 102 | 120 | 132 | 125 | 130 |
| Cure torque | 100 | 114 | 127 | 115 | 132 |
| Coefficient of water absorption (%) | 0.22 | 0.20 | 0.28 | 0.24 | 0.29 |

|  | Comparative Example 11 | Comparative Example 12 |
|---|---|---|
| CEL-2021P | 5 | 25 |
| ECON-1020 | 95 | 75 |
| PR-53195 | 52.9 | 58.8 |
| DBU | 1.26 |  |
| TPP |  | 0.79 |
| Fused silica sphere | 765 |  |
| Crushed silica |  | 711 |
| Carbon black | 2 | 2 |
| Carnauba wax | 2 | 2 |
| Spiral flow | 111 | 114 |
| Torque through curing | 108 | 120 |
| Coefficient of water absorption (%) | 0.57 | 0.89 |

EOCN-1020: Cresol novolak-based epoxy resin (manufactured by Nippon Kayaku Ltd.)
PR-53195: Phenol resin (manufactured by Sumitomo Bakelite Co., Ltd.)
DBU: 1,8-diazabicyclo(5,4,0)undecene-7
TPP: Triphenylphosphine As is evident from Table 4, the cured products in Examples 10 to 13 obtained by using the epoxy resin composition for the encapsulation of electronic parts of the present invention (3) showed low coefficients of water absorption compared with the cured products in Comparative Examples 11 to 12, indicating extremely high quality as epoxy resin compositions for encapsulation of electronic parts.

In addition as it is clear from the spiral flow values in Table 4, the epoxy resin composition for the encapsulation of electric components of the present invention (3) that uses the alicyclic diepoxy compound (a) represented by the general formula (I) is excellent in fluidity, that is, moldability.

Examples and Comparative Examples for Invention (4)

Sample 1 (oil 1 of mixing base in Table 5): polypropylene glycol diacetate (molecular weight: 3,000; kinematic viscosity at 100° C.: 9.8 cSt).

Sample 2 (oil 2 of mixing base in Table 5): a full ester of a mixture of 2-methylbutanoic acid and hexanoic acid (molar ratio=1:1), and pentaerythritol (kinematic viscosity at 100° C.: 4.2 cSt)

Examples 14 to 16 and Comparative Examples 13 to 17

The electrical insulating oils of the compositions shown in Table 5, each of which contained an organic acid as a model, were prepared. 500 g each of the electric insulating oils were transferred into beakers, and stirred with heating at 60° C. The samples were collected in a time course, and used to measure the acid value. The results are shown in Table 6. All examples showed a rapid decrease in acid value.

It is to be noted that the initial acid value of the oil of mixing base was 0.02 in the Sample 1, and 0.001 in the Sample 2.

Examples 17 to 21 and Comparative Examples 18 to 21

In addition, the compositions shown in Table 7 were heated in an autoclave (SUS 316-made) for ten days at 150° C. in air. Kinematic viscosity (unit cSt) and acid value (mgKOH/g) after the heating test were evaluated, respectively.

The oxidation stability was measured in accordance with JIS C2101-93.

TABLE 5

|  | Oil of mixing base | Additive | Addition amount of epoxide | Organic acid | Addition amount of organic acid (% by weight) |
|---|---|---|---|---|---|
| Example 14 | 1 | Epoxy in Example 1 | 3 | Acetic acid | 3 |
| Example 15 | 2 | Epoxy in Example 1 | 3 | Hexanoic acid | 3 |
| Example 16 | 2 | Epoxy in Example 2 | 3 | Hexanoic acid | 5 |
| Comparative Example 13 | 1 | Epoxidized soybean oil | 3 | Acetic acid | 3 |
| Comparative Example 14 | 2 | Epoxidized soybean oil | 3 | Hexanoic acid | 3 |
| Comparative Example 15 | 2 | Phenyl glycidyl ether | 3 | Hexanoic acid | 3 |
| Comparative Example 16 | 1 | Diepoxide of vinyl cyclohexene | 3 | Acetic acid | 3 |
| Comparative Example 17 | 2 | Celloxide 2021 | 3 | Acetic acid | 3 |

An epoxidized soybean oil (DAIMACS-300, manufactured by Daicel Chemical Industries Co., Ltd.) was used as the epoxy compound in each of Comparative Examples 13 and 14.

Phenyl glycidyl ether was used in Comparative Example 15.

Celloxide 2021 in Comparative Example 17 is 3,4-epoxy-cyclohexylmethyl (3,4-epoxy cyclohexane carboxylate) manufactured by Daicel Chemical Industries, Ltd.

TABLE 6

| | Acid value immediately after addition (mgKOH/g) | Acid value after two hours | Acid value after six hours | Acid value after twelve hours |
|---|---|---|---|---|
| Example 14 | 1.98 | 0.86 | 0.13 | 0.05 |
| Example 15 | 1.06 | 0.32 | 0.10 | 0.02 |
| Example 16 | 1.22 | 0.50 | 0.21 | 0.05 |
| Comparative Example 13 | 1.91 | 0.85 | 0.51 | 0.24 |
| Comparative Example 14 | 1.39 | 1.10 | 0.82 | 0.35 |
| Comparative Example 15 | 1.23 | 0.64 | 0.50 | 0.38 |
| Comparative Example 18 | 1.90 | 0.50 | 0.21 | 0.02 |
| Comparative Example 19 | 1.88 | 0.79 | 0.48 | 0.18 |

TABLE 7

| | Oil of mixing base | Additive | Addition amount (% by weight) | Viscosity before the examination | Viscosity after the examination | Acid value before the examination | Acid value after the examination | Oxidation stability Amount of sludge (% by weight) | Total acid value |
|---|---|---|---|---|---|---|---|---|---|
| Example 17 | 1 | Epoxy in Example 1 | 2 | 52 | 52 | 0.01 | 0.02 | 0.08 | 0.26 |
| Example 18 | 1 | Epoxy in Example 1 | 4 | 51 | 51 | 0.01 | 0.01 | 0.10 | 0.24 |
| Example 19 | 2 | Epoxy in Example 2 | 1 | 52 | 51 | 0.01 | 0.02 | 0.11 | 0.46 |
| Example 20 | 1 | Epoxy in Example 3 | 5 | 51 | 51 | 0.01 | 0.02 | 0.12 | 0.20 |
| Example 21 | 2 | Epoxy in Example 3 | 2 | 52 | 52 | 0.01 | 0.03 | 0.10 | 0.27 |
| Comparative Example 18 | 1 | Epoxidized soybean oil | 2 | 50 | 53 | 0.01 | 1.29 | 0.12 | 1.25 |
| Comparative Example 19 | 2 | — | | 53 | 58 | 0.01 | 2.76 | 0.15 | 3.48 |
| Comparative Example 20 | 1 | Diepoxide of vinyl cyclohexene | 2 | 51 | 53 | 0.01 | 0.08 | 0.11 | 0.60 |
| Comparative Example 21 | 2 | Celloxide 2021 | 3 | 52 | 53 | 0.01 | 1.11 | 0.14 | 1.41 |

Celloxide 2021 in Comparative Example 21 is 3,4-epoxy-cyclohexylmethyl (3,4-epoxy cyclohexane carboxylate) manufactured by Daicel Chemical Industries, Ltd.

As shown in Tables 5 to 7, the stabilizers for electrical insulating oils of the present invention (4), i.e. the alicyclic diepoxy compounds represented by the general formula (I) and electrical insulating oils containing the compounds are low in acid value, and the stabilizers improve the properties of insulating oils.

Examples and Comparative Examples for Invention (5)

First, the following alicyclic diepoxy compound (a-1), the epoxy resin (a-2), acid anhydrides 1 and 2, curing accelerators 1 and 2, and inorganic fillers 1 and 2 were prepared.

The alicyclic diepoxy compound obtained in Example 1 was used as the alicyclic diepoxy compound (a-1). Each of the following epoxy resins 2 to 4 were used as the epoxy compound (a-2):

Epoxy resin 2: CEL-2021P (3,4-epoxycyclohexylmethyl-3,4-epoxycyclohexane carboxylate, manufactured by Daicel Chemical Industries, Ltd.)

Epoxy resin 3: YD-128 (a bisphenol A-based epoxy resin, manufactured by Toto Kasei Co., Ltd.; epoxy equivalent: 190; viscosity: 13,600 mPa·s/25° C.).

Epoxy resin 4: HBE-100 (a hydrogenated bisphenol A diglycidyl ether type epoxy resin, manufactured by New Japan Chemical Ltd.; epoxy equivalent: 210; viscosity: 2,210 mPa·s/25° C.)

[Acid anhydride 1] Methylhexahydrophthalic anhydride (trade name RIKACID MH-700: manufactured by New Japan Chemical Co., Ltd.)

[Acid anhydride 2] Methyl norbornene dicarboxylic anhydride (trade name HNA: manufactured by New Japan Chemical Co., Ltd.)

[Curing accelerator 1] Ethylene glycol

[Curing accelerator 2] DBU (diazabicycloundecene)

[Inorganic filler 1] Spherical fused silica (Particles having average particle size of 50 μm or less occupy more than 99% by weight in the entire particles)

[Inorganic filler 2] Fused alumina (Particles having average particle size of 50 μm or less occupy more than 99% by weight in the entire particles)

Examples 17 to 24 and Comparative Examples 22 to 25

Ingredients shown in Tables 8 and 9 were mixed respectively in the ratios shown in the tables. The resulting mixtures were stirred at about 25° C. under reduced pressures (3 to 5 Torr) using a mixer ("Awatorinentaro AR-100", manufactured by THINKY CORPORATION) to obtain insulative casting epoxy resin compositions. The above insulative casting epoxy resin compositions were molded and cured into molded products in a prescribed shape by the casting method, respectively. In Tables 8 and 9, the mixing quantities of the respective ingredients are shown in parts by weight.

TABLE 8

|  | Example 17 | Example 18 | Example 19 | Example 20 | Example 21 | Example 22 | Example 23 | Example 24 |
|---|---|---|---|---|---|---|---|---|
| Epoxy resin a-1 | 50 | 20 | 10 | 50 | 20 | 20 | 75 | 40 |
| Epoxy resin 2 | 50 | 80 | 90 | | | | | |
| Epoxy resin 3 | | | | 50 | 80 | | | |
| Epoxy resin 4 | | | | | | 80 | 25 | 60 |
| Acid anhydride 1 | 132 | 123 | 114 | 50 | 94 | 44 | 126 | 108 |
| Acid anhydride 2 | | | | 63 | | 40 | | |
| Curing accelerator 1 | 2.3 | 2.2 | 2.1 | 2.1 | 1.9 | 1.8 | 2.3 | 2.1 |
| Curing accelerator 2 | 2.3 | 2.2 | 2.1 | 2.1 | 1.9 | 1.8 | 2.3 | 2.1 |
| Filler 1 (% by weight in the composition) | | | | | 220 (52.7) | 220 (54.0) | | 220 (50.9) |
| Filler 2 (% by weight in the composition) | 150 (38.8) | 150 (39.7) | 200 (47.8) | 300 (58.0) | | | 300 (56.5) | |

TABLE 9

|  | Comparative Example 22 | Comparative Example 23 | Comparative Example 24 | Comparative Example 25 |
|---|---|---|---|---|
| Epoxy resin a-1 | | | | |
| Epoxy resin 2 | | | | 5 |
| Epoxy resin 3 | 100 | 95 | | |
| Epoxy resin 4 | | 5 | 100 | 95 |
| Acid anhydride 1 | 81 | 77 | 69 | 71 |
| Acid anhydride 2 | 1.8 | 1.8 | 1.7 | 1.7 |
| Curing accelerator 1 | 1.8 | 1.8 | 1.7 | 1.7 |
| Filler 1 | 220 | 220 | | |
| Filler 2 | | | 300 | 300 |

The casting epoxy resin compositions thus obtained for electrical insulation of the examples and epoxy resin compositions of the comparative examples were cured under prescribed conditions (140° C.×2 hour+170° C.×10 hour). Electrical characteristics (dielectric dissipation factor and permittivity), mechanical properties (bending strength), and glass transition temperatures (Tg) of the cured products were measured under respective experimental conditions shown in the following. Tables 10 and 11 show the results. In any of the following examinations, the values were calculated as the average of five samples.

TABLE 10

|  | Example 17 | Example 18 | Example 19 | Example 20 | Example 21 | Example 22 | Example 23 | Example 24 |
|---|---|---|---|---|---|---|---|---|
| Dielectric dissipation factor (%) | 0.2 | 0.3 | 0.2 | 0.2 | 0.3 | 0.2 | 0.3 | 0.3 |
| Permittivity ($\epsilon$) | 3.5 | 4.0 | 4.1 | 4.1 | 4.0 | 3.8 | 3.2 | 4.2 |
| Bending strength (kg/mm$^2$) | 20 | 21 | 23 | 21 | 22 | 20 | 18 | 19 |
| Tg (° C.) | 241 | 230 | 218 | 215 | 175 | 170 | 218 | 183 |

TABLE 11

|  | Comparative Example 22 | Comparative Example 23 | Comparative Example 24 | Comparative Example 25 |
|---|---|---|---|---|
| Dielectric dissipation factor (%) | 0.3 | 0.4 | 0.3 | 0.3 |
| Permittivity ($\epsilon$) | 5.7 | 5.4 | 4.9 | 4.8 |
| Bending strength (kg/mm$^2$) | 17 | 16 | 14 | 15 |
| Tg (° C.) | 148 | 142 | 129 | 152 |

[Dielectric Dissipation Factor and Permittivity]

Samples of 1 mm thickness×60 mm diameter were made, in which a main electrode and surrounding guard electrodes were formed in one side and a counter electrode was formed on the other side respectively with an electroconductive paint. Those samples were heated to 100° C. in an incubator and their capacitance and conductance (measuring frequency: 50 Hz) were measured respectively by the transformer bridge method. Dielectric dissipation factor (tan δ) and permittivity ($\epsilon$) were calculated from those results by using the following expression.

Dielectric dissipation factor (tan δ)=$Gx/2\pi \cdot f \cdot Cx$

Permittivity ($\epsilon$)=$Cx/C_0$

Cx: Capacitance (pF) when the bridge reaches equilibrium.

$C_0$: Capacitance (pF) at $\epsilon=1$, calculated from area of main electrode and thickness of sample Gx: Conductance (S) of samples f: Measuring frequency (Hz)

[Bending Strength]

Samples were made in 10 mm width×100 mm length×4 mm thickness and held at both ends with a gap of 64 mm. A load was applied to the center of the samples by means of a pressure wedge to determine the maximum load at the time of bending breakage.

[Tg (Glass Transition Temperature: ° C.)]

Samples were made in the size of 5×5×10 mm. According to the thermodilatometry method (using a thermomechanical analyzer TMA/SS6100, manufactured by Seiko Instruments Inc.), the temperature of the samples was increased at 5° C./minute and the dimension changes were plotted. The glass transition temperature (Tg) was obtained as the transition point of the coefficient of thermal expansion.

The results in Tables 10 and 11 indicate that the cured products obtained by curing the casting epoxy resin composition for electrical insulation of the present invention (5) have excellent properties such as high bending strength, high Tg, and low permittivity.

INDUSTRIAL APPLICABILITY

With a specific alicyclic diolefin compound, the alicyclic diepoxy compound represented by the general formula (1) can be produced in high purity, in high yields, and at low cost. A cured product obtained by curing a curable epoxy resin composition containing the alicyclic diepoxy compound and a curing agent, etc., shows very good performance in transparency, heat resistance, and the like, compared with cured products of conventional epoxy resins. The cured product may be used for coatings, ink, adhesives, sealants, encapsulants, and the like. Moreover, the curable epoxy resin composition is useful for a casting epoxy resin composition for electrical insulation and for an epoxy resin composition for encapsulation of electronic parts. Furthermore, the alicyclic diepoxy compound is useful for a stabilizer for an electrical insulating oil.

What is claimed is:

1. A curable epoxy resin composition comprising:
    an alicyclic diepoxy compound (A) represented by the following general formula (I):

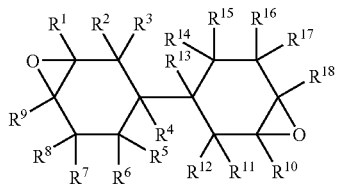

wherein, each of $R^1$ to $R^{18}$, which are the same or different, represents a hydrogen atom, a halogen atom, a hydrocarbon group optionally containing an oxygen atom or a halogen atom, or an alkoxy group that optionally has a substituent group;
    a thermal cationic (b1) or photocationic (b2) polymerization initiator (B) or an acid anhydride (C); and, optionally,
    an additional epoxy resin (D).

2. A curable epoxy resin composition according to claim 1, wherein the alicyclic diepoxy compound represented by the formula (I) comprises bicyclohexyl-3,3'-diepoxide.

3. A curable epoxy resin composition according to claim 1, wherein the photocationic polymerization initiator comprises a sulfonium salt-based photocationic polymerization initiator.

4. A curable epoxy resin composition according to claim 1, wherein the acid anhydride comprises methylhexahydrophthalic anhydride.

5. A cured product obtained by curing the curable epoxy resin composition according to claim 1.

6. An epoxy resin composition for encapsulation of electronic parts, comprising:
    an alicyclic diepoxy compound (a) represented by the following general formula (I):

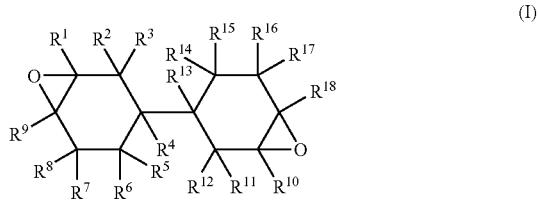

wherein, each of $R^1$ to $R^{18}$, which are the same or different, represents a hydrogen atom, a halogen atom, a hydrocarbon group optionally containing an oxygen atom or a halogen atom, or an alkoxy group that optionally has a substituent group;
    a curing agent (b);
    a curing accelerator (c);
    an inorganic filler (d); and
    an additional epoxy resin (e),
wherein components (a) and (b) are essential ingredients, while components (c), (d), and (e) are optional ingredients.

7. An epoxy resin composition for encapsulation of electronic parts according to claim 6, wherein the alicyclic diepoxy compound (a) represented by the formula (I) comprises bicyclohexyl-3,3'-diepoxide.

8. An epoxy resin composition for encapsulation of an electric component according to claim 6, wherein the curing agent (b) comprises at least one selected from the group consisting of an amine-based curing agent, an acid anhydride-based curing agent, and a phenol-based resin.

9. An epoxy resin composition for encapsulation of electronic parts according to claim 6, wherein the additional epoxy resin (e) comprises a cresol novolak-based epoxy resin.

10. A cured product obtained by curing the epoxy resin composition for encapsulation of electronic parts according to claim 6.

11. A casting epoxy resin composition for electrical insulation, comprising a thermocuring resin and an inorganic filler, characterized in that:
    the thermocuring resin includes:
    (A) an epoxy resin composition composed of 5 to 80% by weight of an alicyclic diepoxy compound (a-1) represented by the following general formula (I):

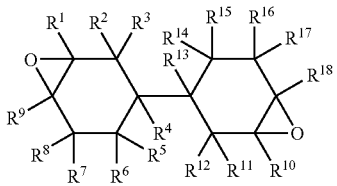

(I)

wherein, each of $R^1$ to $R^{18}$, which are the same or different, represents a hydrogen atom, a halogen atom, a hydrocarbon group optionally containing an oxygen atom or a halogen atom, or an alkoxy group that optionally has a substituent group, 95 to 20% by weight of an epoxy compound (a-2) other than the alicyclic diepoxy compound (a-1) represented by the formula (I) [total of the alicyclic diepoxy compound (a-1) and the epoxy compound (a-2) is 100% by weight];

(B) an acid anhydride; and
(C) a curing accelerator;

and the thermocuring resin further contains:

(D) the inorganic filler; and
a mixing ratio of the ingredient (B) is in a range of 0.6 to 1.0 equivalent based on 1 equivalent of the ingredient (A), a mixing ratio of the ingredient (C) is 0.5 to 10 parts by weight relative to 100 parts weight of the (A) and (B) in total, and a mixing ratio of the ingredient (D) is 30 to 80% by weight of a total amount of the ingredients (A) to (D).

12. A casting epoxy resin composition for electrical insulation according to claim 11, wherein the alicyclic diepoxy compound (a-1) represented by the general formula (I) comprises bicyclohexyl-3,3'-diepoxide.

13. A casting epoxy resin composition for electrical insulation according to claim 11, wherein the acid anhydride comprises methylhexahydrophthalic anhydride or methyl norbornene dicarboxylic anhydride.

14. A casting epoxy resin composition for electrical insulation according to claim 11, wherein the curing accelerator comprises ethylene glycol or diazabicycloundecene.

15. A casting epoxy resin composition for electrical insulation according to claim 11, wherein the inorganic filler comprises a spherical fused silica or fused alumina.

16. A casting epoxy resin composition for electrical insulation according to claim 11, wherein the epoxy compound (a-2) comprises at least one of 3,4-epoxycyclohexylmethyl-3,4-epoxy cyclohexane carboxylate, a bisphenol-based epoxy resin, and a novolak phenol-based epoxy resin.

17. A cured product obtained by curing the casting epoxy resin composition for electrical insulation according to any one of claims 11 to 16.

* * * * *